(12) United States Patent
Sabatino

(10) Patent No.: US 12,138,106 B2
(45) Date of Patent: *Nov. 12, 2024

(54) ACQUIRING AND PROCESSING ACOUSTIC ENERGY EMITTED BY AT LEAST ONE ORGAN IN A BIOLOGICAL SYSTEM

(71) Applicant: Michael E. Sabatino, Broken Arrow, OK (US)

(72) Inventor: Michael E. Sabatino, Broken Arrow, OK (US)

(*) Notice: Subject to any disclaimer, the term of this patent is extended or adjusted under 35 U.S.C. 154(b) by 233 days.

This patent is subject to a terminal disclaimer.

(21) Appl. No.: 17/742,192

(22) Filed: May 11, 2022

(65) Prior Publication Data

US 2022/0265240 A1 Aug. 25, 2022

Related U.S. Application Data

(63) Continuation of application No. 14/524,810, filed on Oct. 27, 2014, now Pat. No. 11,357,471, which is a continuation of application No. 13/430,561, filed on Mar. 26, 2012, now Pat. No. 8,870,791, which is a continuation of application No. 11/602,017, filed on Nov. 20, 2006, now Pat. No. 8,920,343.

(60) Provisional application No. 60/785,357, filed on Mar. 23, 2006.

(51) Int. Cl.
*A61B 5/00* (2006.01)
*A61B 7/00* (2006.01)
*A61B 7/04* (2006.01)

(52) U.S. Cl.
CPC .............. *A61B 7/04* (2013.01); *A61B 5/0022* (2013.01); *A61B 5/7257* (2013.01); *A61B 5/742* (2013.01); *A61B 7/00* (2013.01)

(58) Field of Classification Search
CPC ....... A61B 7/04; A61B 5/0022; A61B 5/7257; A61B 5/742; A61B 7/00
See application file for complete search history.

(56) References Cited

U.S. PATENT DOCUMENTS

| | | | | |
|---|---|---|---|---|
| 3,990,435 A | * | 11/1976 | Murphy | A61B 7/003 346/33 ME |
| 4,207,622 A | * | 6/1980 | Miller | G01S 3/8083 367/126 |
| 4,528,689 A | * | 7/1985 | Katz | A61B 7/04 704/211 |
| 4,889,132 A | * | 12/1989 | Hutcheson | A61B 5/02208 600/496 |

(Continued)

OTHER PUBLICATIONS

Campbell-Smith, Patricia E., *Audio Evolution Diagnostics, Inc v. United States, and Globalmedia Group, LLC*, Motion to Dismiss, Jul. 1, 2022, pp. 1-19, United States Court of Federal Claims, United States of America.

*Primary Examiner* — May A Abouelela
(74) *Attorney, Agent, or Firm* — Hall Estill Law Firm

(57) ABSTRACT

In some embodiments, an apparatus for acquiring, processing and transmitting physiological sounds, which may include acoustic sounds from at least one organ in a biological system, may include a sensor for acquiring physiological sounds. Analogue signals representative of the physiological sounds are converted into an electrical output. The electrical output is converted to digital data. A processing unit processes the digital data in a manner selected by a user. A display device displays the digital data and can be customized by a user.

20 Claims, 30 Drawing Sheets

(56) References Cited

U.S. PATENT DOCUMENTS

| | | | | |
|---|---|---|---|---|
| 4,989,611 A * | 2/1991 | Zanetti | A61B 5/11 | 600/500 |
| 5,989,193 A * | 11/1999 | Sullivan | A61B 5/113 | 600/534 |
| 6,423,013 B1 * | 7/2002 | Bakker | A61B 7/00 | 600/529 |
| 6,572,544 B1 * | 6/2003 | Carter | A61B 5/333 | 607/18 |
| 6,699,204 B1 * | 3/2004 | Kehyayan | A61B 7/003 | 600/533 |
| 7,570,979 B2 * | 8/2009 | Cooper | A61B 5/4818 | 600/323 |
| 7,998,091 B2 * | 8/2011 | Carim | G01N 29/14 | 600/534 |
| 8,323,190 B2 * | 12/2012 | Vitiello | A61B 5/225 | 600/300 |
| 8,398,560 B2 * | 3/2013 | Elser | A61B 5/01 | 600/595 |
| 8,771,204 B2 * | 7/2014 | Telfort | A61B 7/04 | 600/528 |
| 2003/0002685 A1 * | 1/2003 | Werblud | A61B 7/04 | 600/528 |
| 2004/0039294 A1 * | 2/2004 | Sullivan | A61B 7/04 | 600/528 |
| 2004/0230128 A1 * | 11/2004 | Brockway | A61N 1/36585 | 600/510 |
| 2005/0043643 A1 * | 2/2005 | Priemer | A61B 7/026 | 600/528 |
| 2005/0113703 A1 * | 5/2005 | Farringdon | A61B 5/021 | 600/509 |
| 2005/0124864 A1 * | 6/2005 | Mack | A61B 5/6892 | 600/587 |
| 2005/0234314 A1 * | 10/2005 | Suzuki | A61B 5/0205 | 600/595 |
| 2006/0020220 A1 * | 1/2006 | Bostian | G16H 50/50 | 600/528 |
| 2006/0281975 A1 * | 12/2006 | Yang | A61B 5/00 | 600/300 |
| 2007/0003072 A1 * | 1/2007 | Ward | A61B 7/00 | 381/71.1 |
| 2007/0176826 A1 * | 8/2007 | Daniele | G01S 5/0289 | 342/465 |
| 2007/0208232 A1 * | 9/2007 | Kovacs | A61B 5/1118 | 600/595 |
| 2008/0214903 A1 * | 9/2008 | Orbach | G16H 40/67 | 705/2 |
| 2008/0243112 A1 * | 10/2008 | De Neve | A61F 7/123 | 607/105 |
| 2008/0281220 A1 * | 11/2008 | Sharifpour | A61B 5/411 | 600/538 |
| 2009/0149699 A1 * | 6/2009 | Ullmann | A61M 21/02 | 600/28 |
| 2011/0015493 A1 * | 1/2011 | Koschek | A61B 5/02 | 600/300 |

* cited by examiner

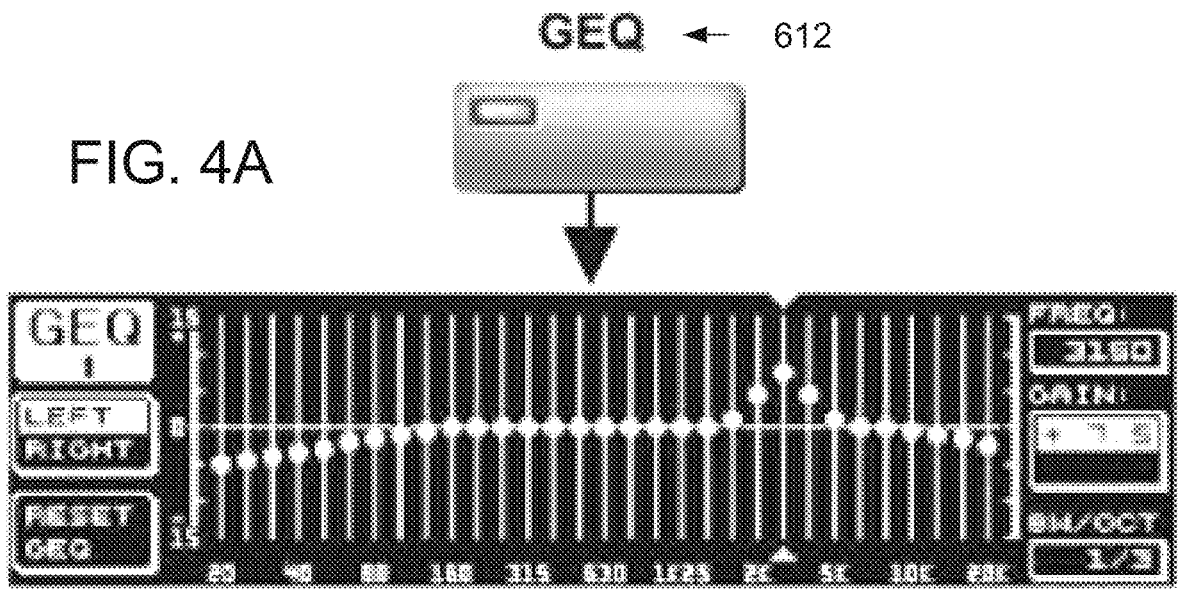
FIG. 4A
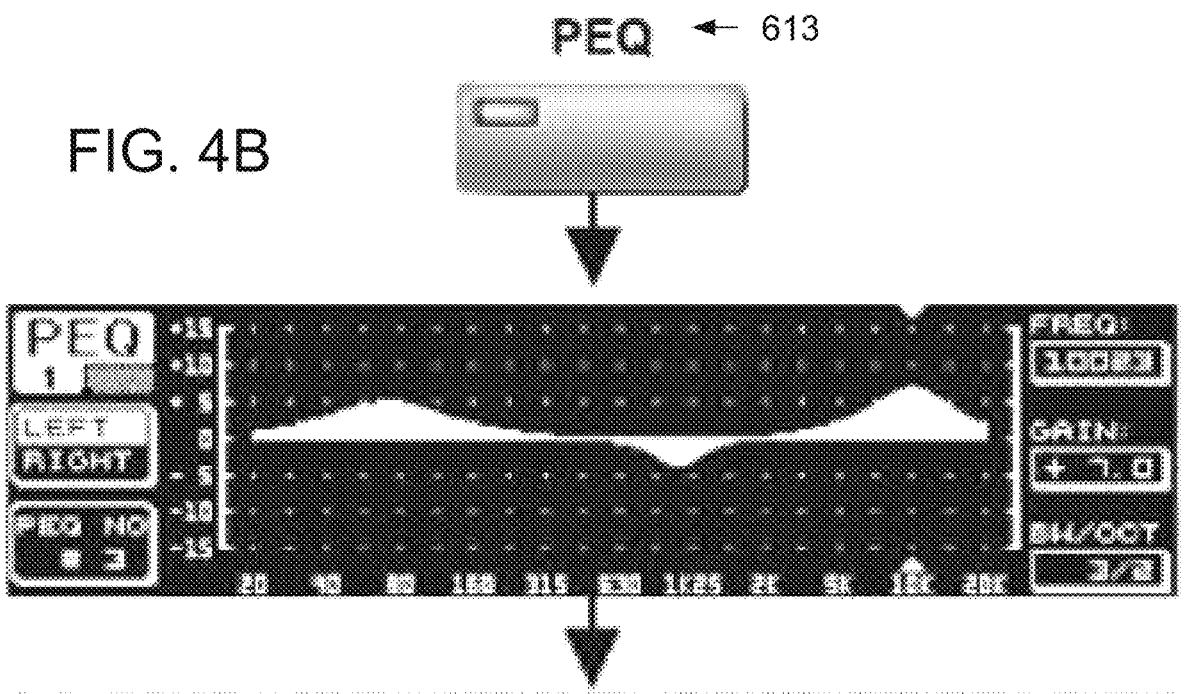
FIG. 4B

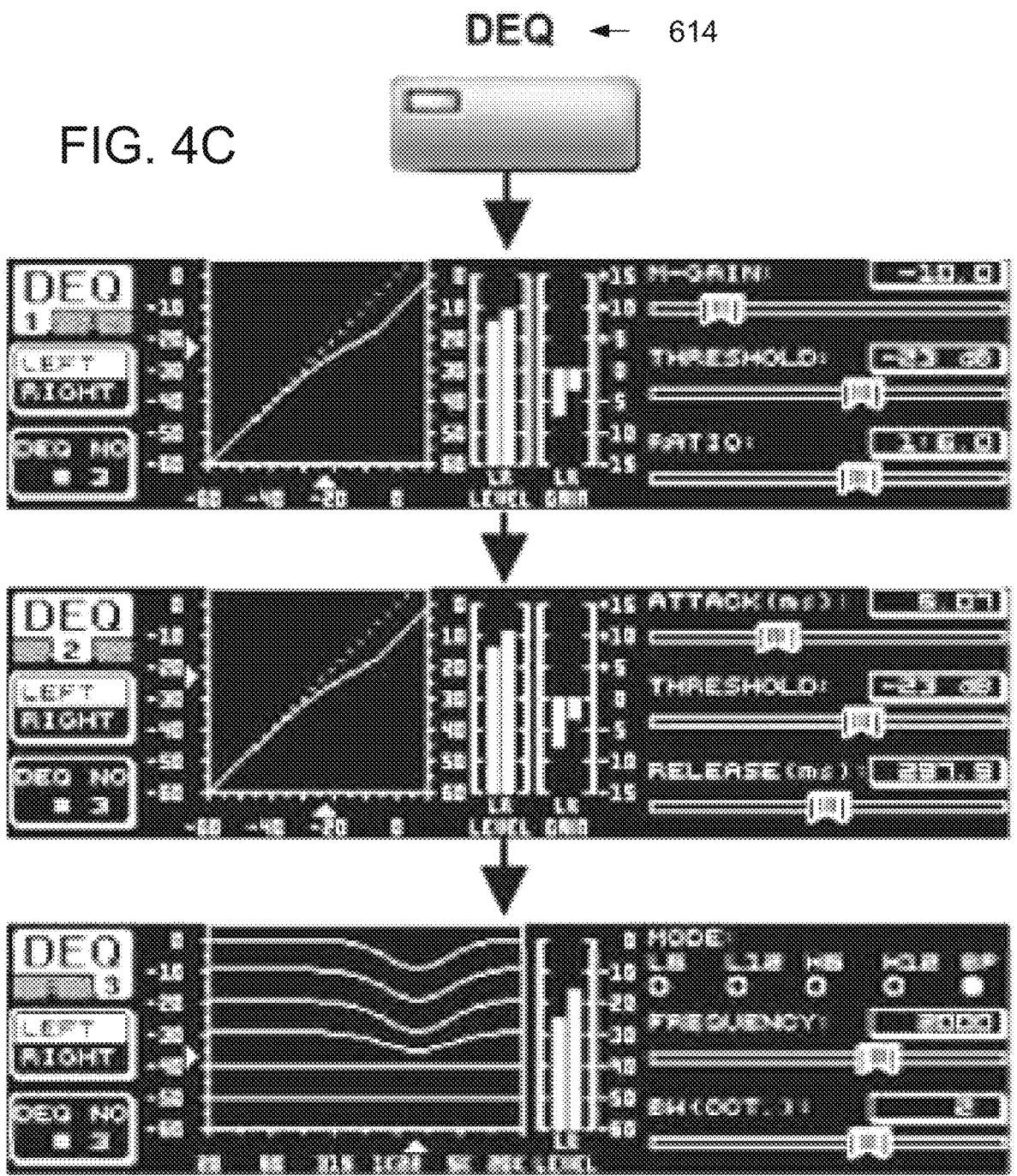

FIG. 4E
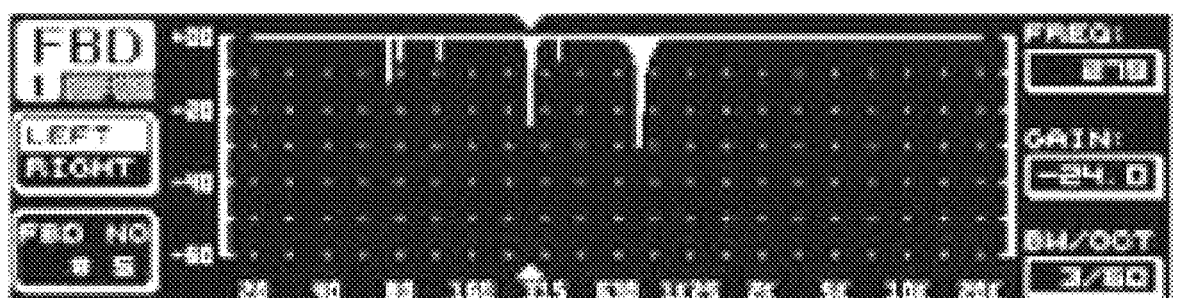
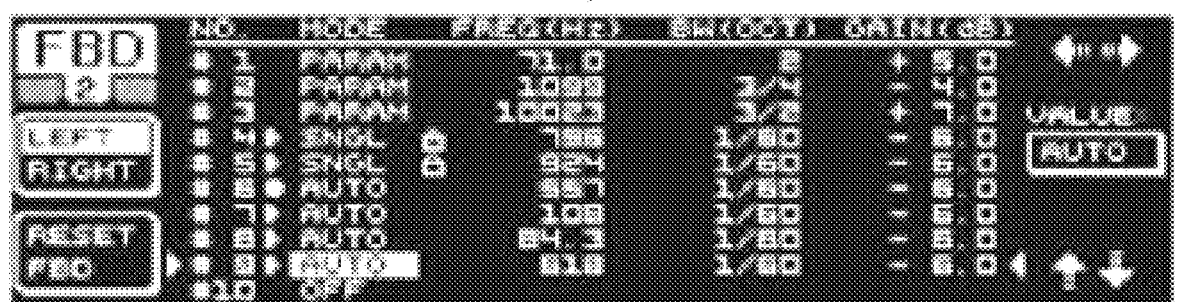

FIG. 4F
DYN ← 615
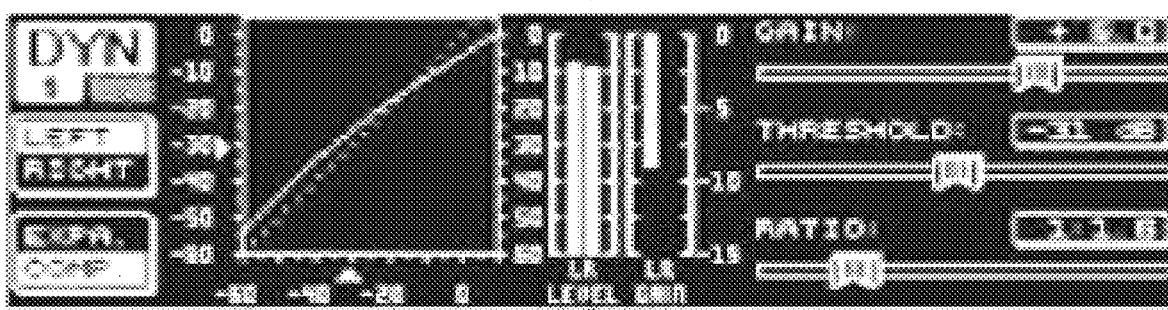
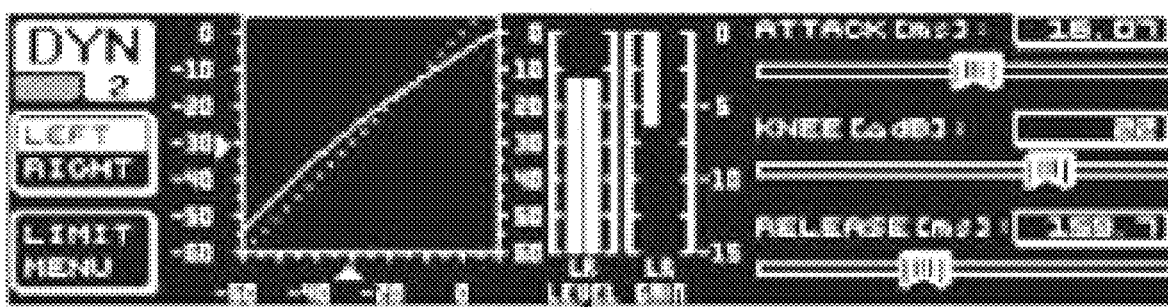
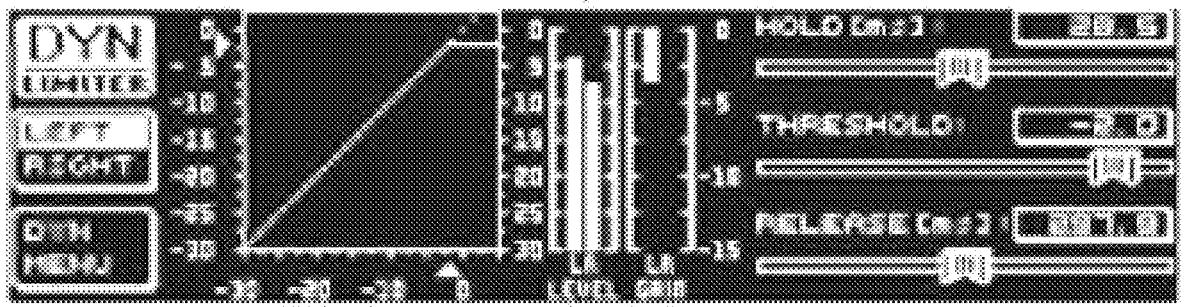

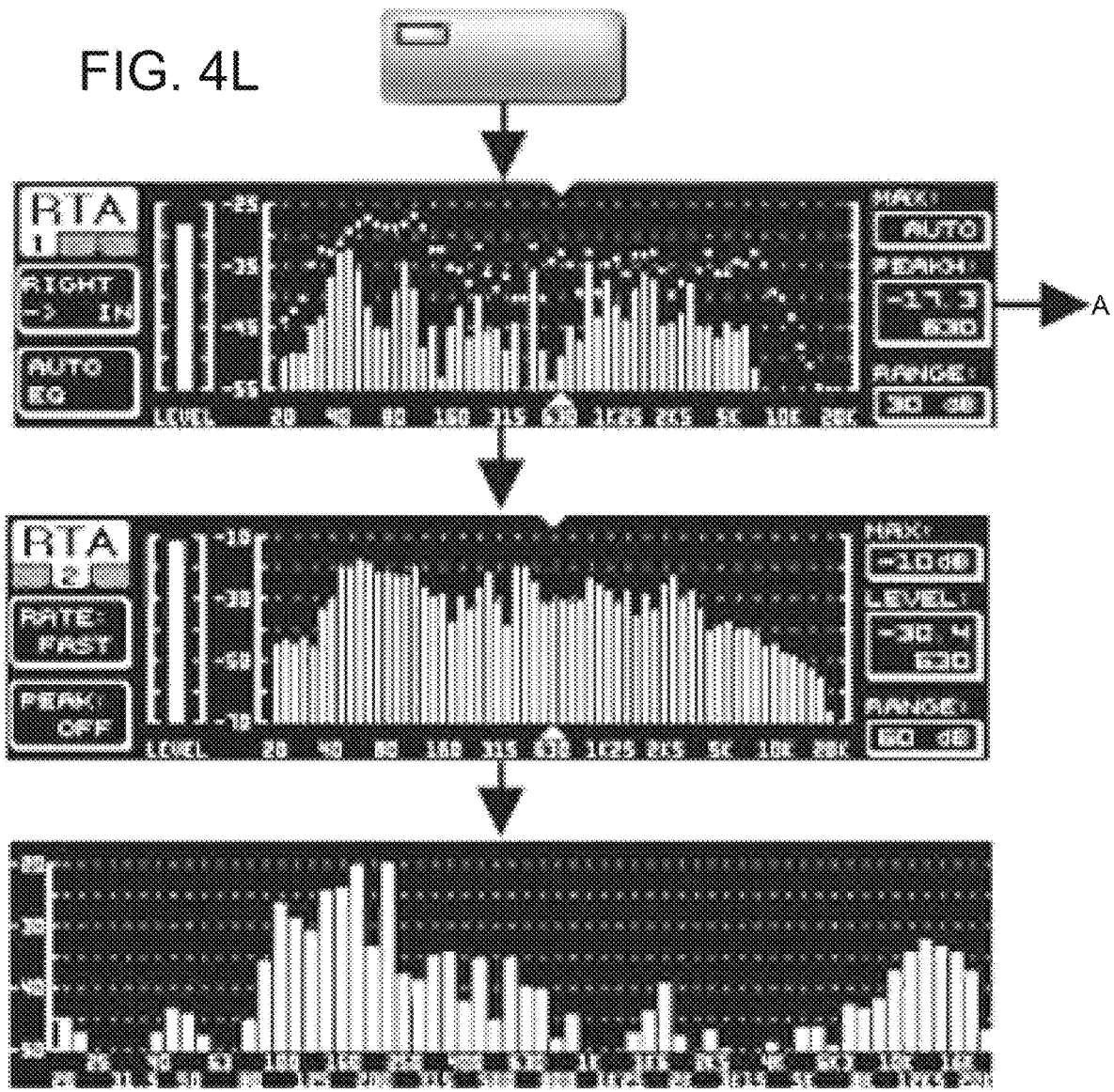

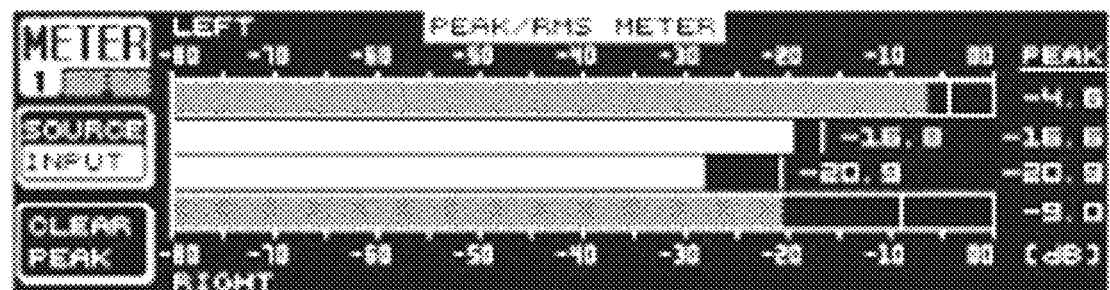
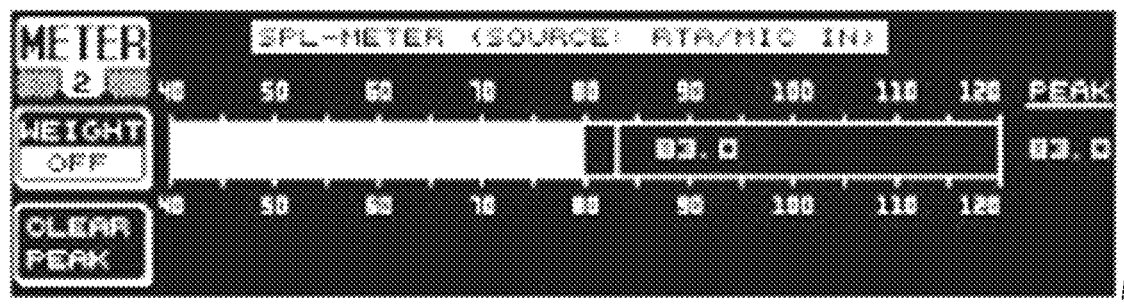
622A
FIG. 5

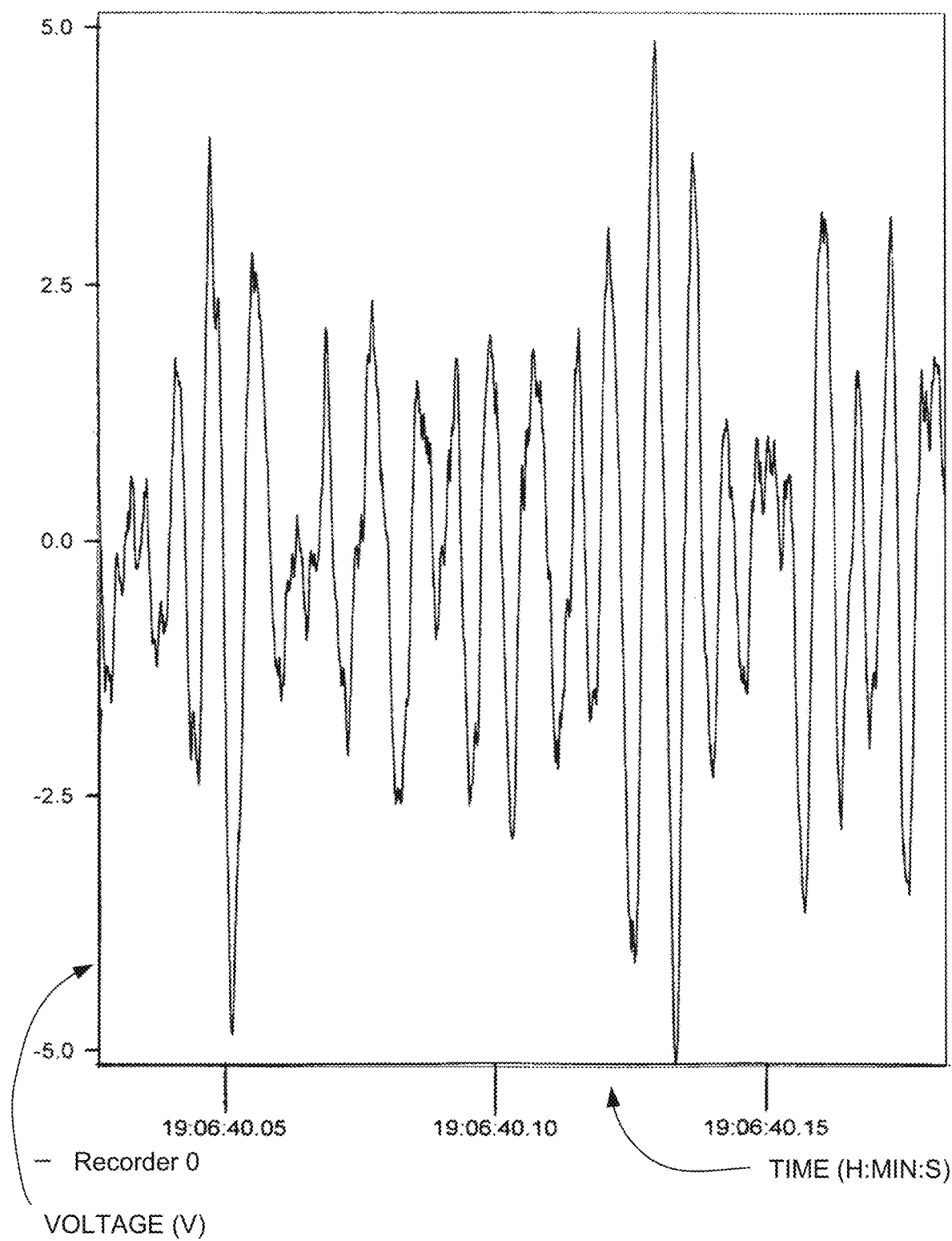

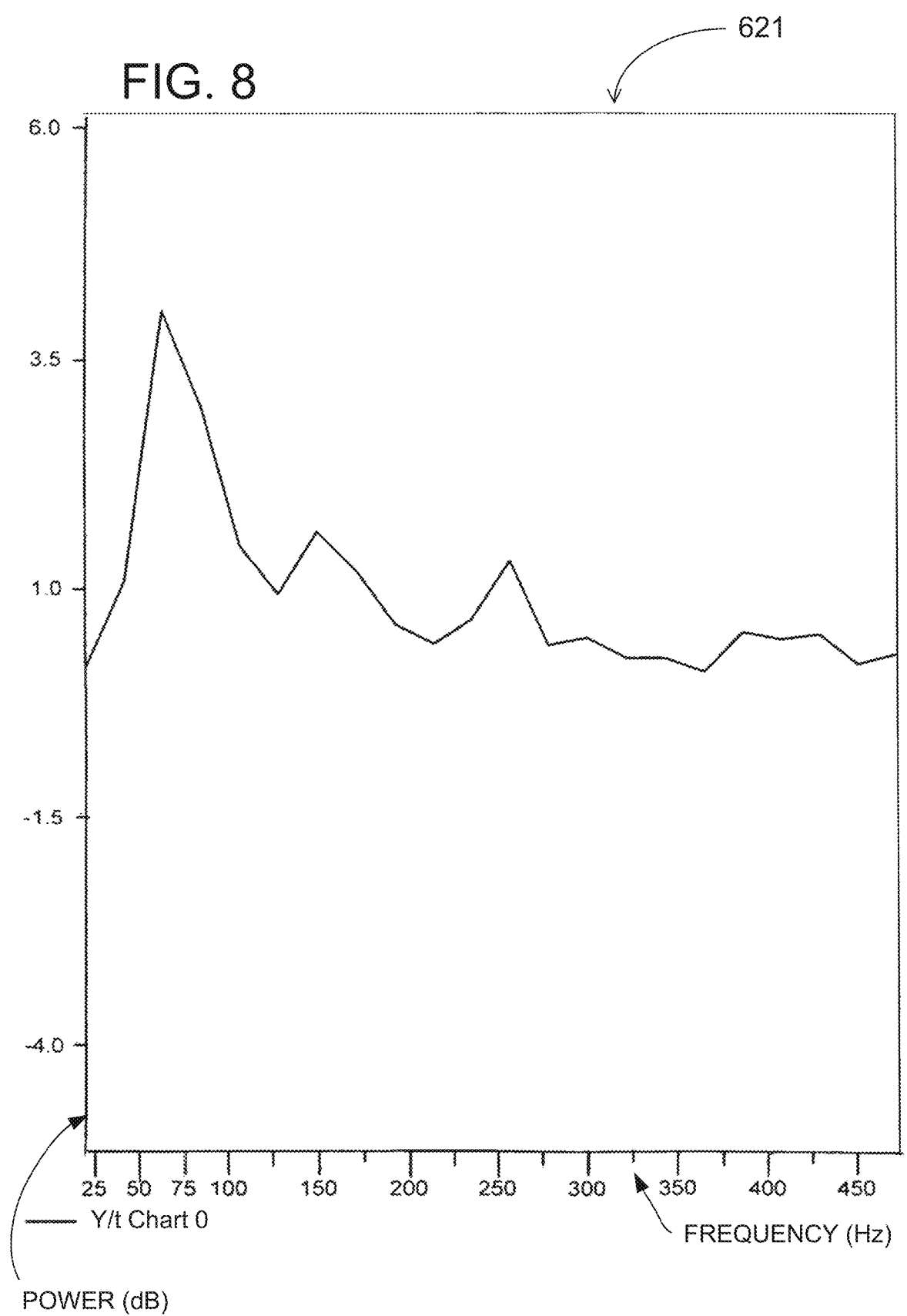

FIG. 9

| Number | List 0 |
|---|---|
| 0 | 0.32416 |
| 1 | 0.24833 |
| 2 | 0.26159 |
| 3 | 0.38564 |
| 4 | 0.39383 |
| 5 | 0.27714 |
| 6 | 0.33288 |
| 7 | 0.28556 |
| 8 | 0.36188 |
| 9 | 0.39170 |
| 10 | 0.41769 |
| 11 | 0.37412 |
| 12 | 0.28504 |
| 13 | 0.31108 |
| 14 | 0.30409 |
| 15 | 0.30258 |
| 16 | 0.24723 |
| 17 | 0.30873 |
| 18 | 0.44627 |
| 19 | 0.40087 |
| 20 | 0.33600 |
| 21 | 0.31696 |
| 22 | 0.39488 |
| 23 | 0.38666 |

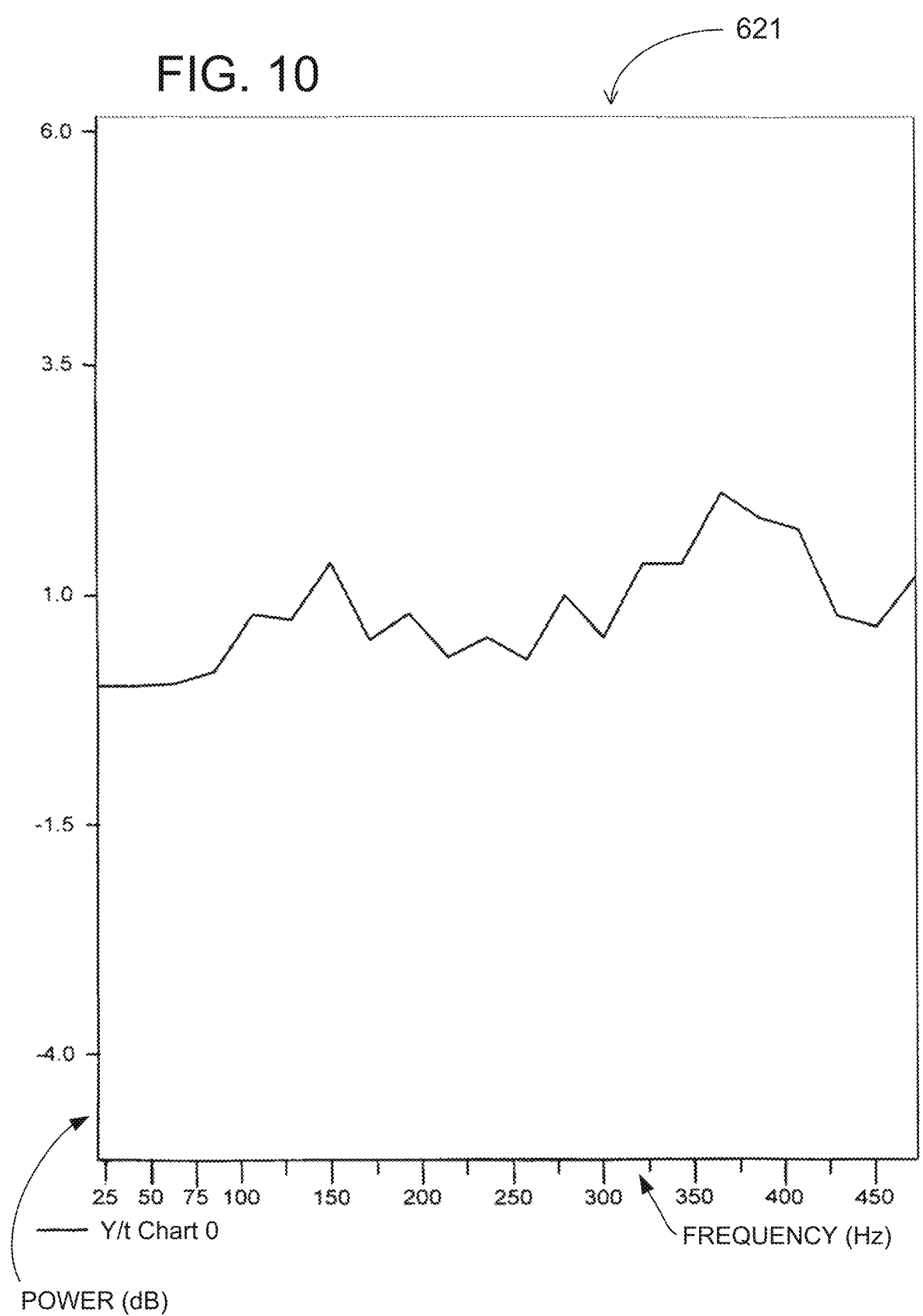

FIG. 11A

| Number | List 0 |
|---|---|
| 144 | 0.16453 |
| 145 | 0.19866 |
| 146 | 0.25353 |
| 147 | 0.30213 |
| 148 | 0.27350 |
| 149 | 0.32605 |
| 150 | 0.38357 |
| 151 | 0.38844 |
| 152 | 0.39335 |
| 153 | 0.40621 |
| 154 | 0.36097 |
| 155 | 0.36865 |
| 156 | 0.34936 |
| 157 | 0.35348 |
| 158 | 0.37133 |
| 159 | 0.38622 |
| 160 | 0.37478 |
| 161 | 0.35564 |
| 162 | 0.37702 |
| 163 | 0.36008 |
| 164 | 0.36676 |
| 165 | 0.36367 |
| 166 | 0.34848 |
| 167 | 0.34179 |
| 168 | 0.35888 |
| 169 | 0.31170 |
| 170 | 0.34592 |
| 171 | 0.36733 |
| 172 | 0.35863 |
| 173 | 0.34091 |
| 174 | 0.33474 |
| 175 | 0.36267 |
| 176 | 0.36828 |
| 177 | 0.34860 |
| 178 | 0.35901 |
| 179 | 0.36568 |
| 180 | 0.34046 |
| 181 | 0.33658 |
| 182 | 0.34959 |
| 183 | 0.29098 |
| 184 | 0.33565 |

FIG. 11B

| Number | List 0 |
|---|---|
| 185 | 0.32099 |
| 186 | 0.30145 |
| 187 | 0.34859 |
| 188 | 0.34272 |
| 189 | 0.37439 |
| 190 | 0.32083 |
| 191 | 0.31364 |
| 192 | 0.17720 |
| 193 | 0.29043 |
| 194 | 0.34371 |
| 195 | 0.36921 |
| 196 | 0.37567 |
| 197 | 0.38466 |
| 198 | 0.36238 |
| 199 | 0.35867 |
| 200 | 0.34770 |
| 201 | 0.33068 |
| 202 | 0.35571 |
| 203 | 0.29219 |
| 204 | 0.32458 |
| 205 | 0.36456 |
| 206 | 0.34355 |
| 207 | 0.38699 |

FIG. 12B

| Number | List 0 |
|---|---|
| 24 | 0.578 |
| 25 | 1.728 |
| 26 | 1.008 |
| 27 | 0.558 |
| 28 | 0.880 |
| 29 | 0.944 |
| 30 | 1.019 |
| 31 | 0.602 |
| 32 | 0.532 |
| 33 | 0.850 |
| 34 | 1.071 |
| 35 | 1.244 |
| 36 | 0.553 |
| 37 | 0.601 |
| 38 | 0.550 |
| 39 | 0.637 |
| 40 | 1.164 |
| 41 | 0.548 |
| 42 | 0.682 |
| 43 | 1.525 |
| 44 | 2.146 |
| 45 | 1.216 |
| 46 | 0.462 |
| 47 | 0.429 |
| 48 | 0.199 |
| 49 | 0.407 |
| 50 | 0.629 |
| 51 | 0.589 |
| 52 | 0.803 |
| 53 | 0.596 |
| 54 | 0.473 |
| 55 | 0.239 |
| 56 | 0.699 |
| 57 | 1.176 |
| 58 | 1.875 |
| 59 | 0.982 |
| 60 | 0.267 |
| 61 | 0.854 |
| 62 | 1.341 |
| 63 | 0.253 |
| 64 | 0.584 |

FIG. 12C

| Number | List 0 |
|---|---|
| 65 | 1.380 |
| 66 | 1.579 |
| 67 | 0.614 |
| 68 | 0.793 |
| 69 | 0.249 |
| 70 | 0.626 |
| 71 | 0.517 |
| 72 | 0.692 |
| 73 | 0.843 |
| 74 | 0.237 |
| 75 | 0.996 |
| 76 | 0.536 |
| 77 | 0.344 |
| 78 | 1.064 |
| 79 | 1.493 |
| 80 | 0.816 |
| 81 | 0.100 |
| 82 | 0.440 |
| 83 | 1.676 |
| 84 | 0.877 |
| 85 | 0.423 |
| 86 | 0.724 |
| 87 | 1.066 |

ACQUIRING AND PROCESSING ACOUSTIC ENERGY EMITTED BY AT LEAST ONE ORGAN IN A BIOLOGICAL SYSTEM

RELATED APPLICATIONS

This application is a continuation of copending U.S. patent application Ser. No. 14/524,810 filed Oct. 27, 2014, entitled "ACQUIRING AND PROCESSING ACOUSTIC ENERGY EMITTED BY AT LEAST ONE ORGAN IN A BIOLOGICAL SYSTEM, which claimed priority to U.S. patent application Ser. No. 13/430,561 filed Mar. 26, 2012, entitled "APPARATUS FOR ACQUIRING, PROCESSING AND TRANSMITTING PHYSIOLOGICAL SOUNDS," which claimed priority to copending U.S. patent application Ser. No. 11/602,017 filed Nov. 20, 2006 entitled, "SYSTEM AND METHOD FOR ACQUISITION AND ANALYSIS OF PHYSIOLOGICAL AUDITORY SIGNALS," which claimed priority to U.S. Prov. Pat. App. No. 60/785,357 filed on Mar. 23, 2006, entitled "SYSTEM AND METHOD FOR ACQUISITION AND ANALYSIS OF PHYSIOLOGICAL AUDITORY SIGNALS." All of the contents of U.S. patent application Ser. No. 14/524,810, U.S. patent application Ser. No. 13/430,561, U.S. patent application Ser. No. 11/602, 017, and U.S. Prov. Pat. App. No. 60/785,357 are incorporated herein by reference.

BACKGROUND

Throughout this application, various publications are referenced. The disclosures of these publications in their entireties are hereby incorporated by reference into this application in order to more fully describe the state of the art as known to those skilled therein, as of the date of the disclosure described and claimed herein.

Auscultation of the lung and heart is probably the most widely used physical diagnostic method in respiratory and cardiac disease. However, due to the limitations of the human auditory system, auscultation has such low sensitivity and specificity that many physicians no longer rely solely on it as a diagnostic tool. Although digital acquisition and analysis of physiologic sounds has the potential to be of tremendous diagnostic/therapeutic benefit to patients, the medical community has been slow to embrace this technology. In order to overcome this obstacle, any system for digital acquisition and analysis of physiologic sounds must be lightweight and easy for individuals without technical expertise to operate and modify. In addition, all generated results must be presented in a format that allows for rapid interpretation and correlation with important physiologic values obtained from other tests.

Physiologic sounds may be captured electronically, processed, and transmitted back to the clinician thus enabling the human auditory system to obtain greater information conveyed by the signal. For example, U.S. Pat. No. 5,774, 563 discloses a device for acquiring physiologic sounds. Electronic circuitry embedded in the device enables the operator to filter and amplify the incoming signal. Furthermore, this device also allows the user to listen to the post-processed signal through implementation of earpieces. However, no plan is described for enabling clinicians of ordinary ability to modify the system. Thus, the effective frequency range measured by this device is 70-480 Hz, which is essentially unalterable, has minimal clinical applications. In addition, this system does not provide a means for digital acquisition/display/analysis of the recorded signal, which serves to severely limit the use of this device in a clinical setting. Other forms of analogous art, which are based on these same principles, share similar disadvantages.

Analogous inventions in the art have depicted devices capable of acquiring, processing and digitally recording/analyzing physiologic signals. U.S. Pat. No. 6,139,505 discloses an electronic stethoscope for the digital acquisition and analysis of physiologic sounds. The device consists of a microphone, which can be embedded inside conventional chest pieces. After amplification and filtering, the signal is transferred to an analogue to digital converter (A/D converter) for computer analysis. The system disclosed contains a modifiable number of independent transducers to record physiologic sounds at any particular location, which the operator desires. The device allows for amplification/filtering of the recorded signal, store these recordings in memory, perform root mean square (RMS) and time expanded waveform analysis, and display data on a monitor for visual analysis/printing. This device is also fairly easy to modify/upgrade/repair and includes a built in program for analyzing respiratory sounds and generating a probable diagnosis based on this information.

However, this device does not disclose a method to enable the physicians to listen to the sound as it is being recorded, but instead, requires them to discern phases of the respiratory cycle simply by inspection of the time expanded waveform. The patent describes a method by which physiologic sound may be processed and transmitted to a computer workstation using analogue circuitry which is bulky and not easily customized thus limiting the device's practical application. Further, no information is given about how this device can be used for higher level analysis (such as performance of Fourier Transformation or wavelet) of the desired signal, only time expanded waveform analysis and RMS of the complete spectrum are illustrated. These quantities give incomplete information regarding the sound and the program is not easily operated/modified by a clinician of ordinary skill. Lastly, no method is outlined by the inventors for reducing the corruption of the data from inadvertent pickup of ambient noise or superimposed signals emitted from other organs in close proximity to the transducer. The probable diagnosis product available with this device is also extremely limited since it provides no quantitative information regarding the degree of functionality of the desired organ system. Although Murphy's electronic stethoscope represents significant improvement from analogous art as a system for the display and analysis of physiologic sounds, the limitations of this device as described above decrease its usefulness in a clinical setting.

Additional devices have been patented which attempt to provide more sophisticated means for mathematically analyzing physiologic sounds and transmitting results to remote locations. One such example can be found in U.S. Pat. No. 6,699,204, which illustrates a device for recording physiologic sound using multiple sensors that are secured to a patient via a harness. Physiologic sound can be recorded by the sensors and relayed to a processing station for filtering/amplification using analogue circuits. The signal is then transferred to a sampler Ech (sound card) for digital recording via analogue circuitry or modem (not shown). With the aid of a specialized calculation manager (Matlab(R) for example), the device can evaluate a set of transformed intensity levels, each associated with a predetermined sound frequency and means for storing each transformed intensity level in correspondence with an associated frequency for the purpose of displaying these intensity levels, transformed on the basis of frequencies as a spectral representation of the auscultation sound.

The device depicted by Kehyayan et al. is a further improvement over analogous art since it provides an accurate spectral representation of the auscultation sound as the intensity varies with time. However, a physician of ordinary ability cannot be expected to have the technical expertise necessary to easily operate and/or modify this analysis program in order to examine a wide array of physiologic sounds. Also, no plan is outlined by the inventor for preventing extraneous sounds (from ambient noise or sound emitted from other organs) from influencing the results displayed on the spectral plots. Lastly, the spectral plots contain too much information for a clinician to interpret in a timely manner. Thus, it is unlikely that the invention proposed by Kehyayan will be useful in a practical setting, and thereby widely embraced by the medical community.

SUMMARY

Various embodiments of the present invention are generally directed to acquiring, processing and transmitting acoustic energy data.

In accordance with various embodiments, acquiring, processing and transmitting acoustic energy data is provided. A sensor for acoustic energy is utilized to convert analogue signals into an electrical output. The electrical output is converted to digital data. The digital data is processed by use of a processing unit. Transmission of the digital data is initiated over a wireless network. Electrical current is supplied to the processing unit through a battery.

These and other features and advantages which characterize the various embodiments of the present invention can be understood in view of the following detailed discussion and the accompanying drawings.

BRIEF DESCRIPTION OF THE DRAWINGS

FIGS. 4A-4L illustrates a variety of operations which may be performed on the acquired data by the digital signal processor.

FIG. 5 illustrates a display of the RMS values for the incoming signal (ambient noise) received from the test microphone. These values can be helpful in quantifying the effect of ambient noise on the calculation of the RMS values of the desired signal.

FIGS. 7A and 7B represent time expanded waveforms of physiologic sounds.

FIG. 8 is a graphical representation of the power spectrum density calculated using the Fast Fourier transformation from an incoming data stream representative of physiologic sounds received by the transducer positioned over the heart.

FIG. 9 depicts the sequential display of RMS values calculated from the PSD after processing for heart sounds. This data may then be used to assess the degree of functionality of the target organ.

FIG. 10 depicts the PSD calculated from tracheal breath sounds using the FFT.

FIGS. 11A and 11B depict the sequential display of RMS values calculated from the PSD after processing of the tracheal breath sound.

FIGS. 12A-12C depict the sequential display of values corresponding to the maximum frequency 12A and corresponding intensity 12B/12C from the desired portions of the PSD after processing of the incoming signal from the heart. Data is displayed as it is obtained from each incoming block.

DETAILED DESCRIPTION

Figure 1:
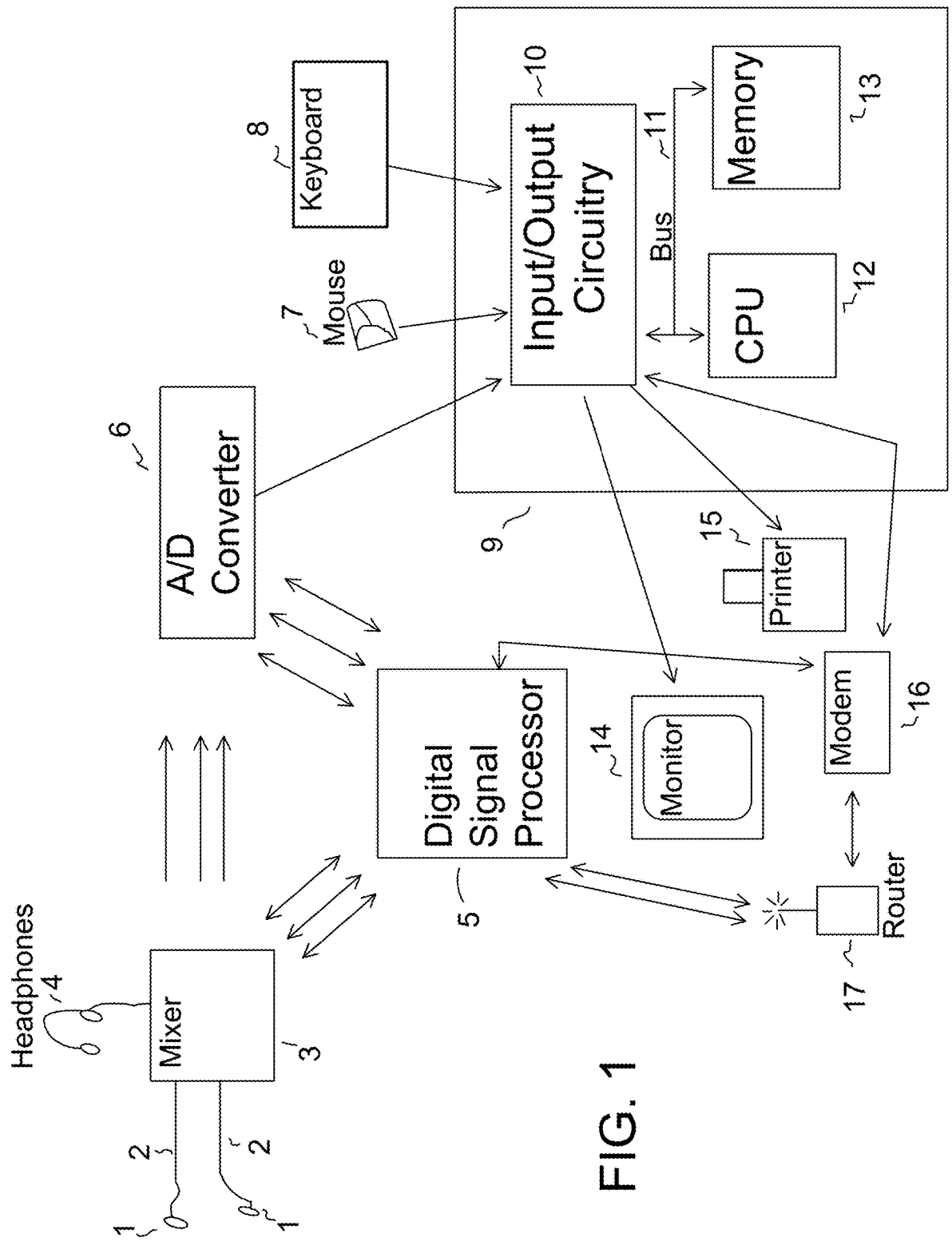
FIG. 1 provides a general overview of an exemplary embodiment disclosed.

It has been proven that organs in the human body emit characteristic physiologic signals when they are functioning in the absence of pathology.

One of the main obstacles to widespread acceptance of electronic stethoscopes is that these devices are too cumbersome, and also, too complicated for health care professionals to operate in a professional setting. A compact, customizable device may be useful. But most important, the device will be an improvement over analogous art by providing a simple interface which allows medical professionals with limited technical background to easily manipulate vital parameters such as block length, overlap, sampling rate, low/high pass filtering, adjusting the Fast Fourier Transformation (FFT) and RMS analysis to cover any component of the frequency spectrum, and applying data windows without the need for computer programming knowledge.

It may be useful boost the accuracy of recording physiological sounds by providing the physician with an efficient method of eliminating background noise (which is either present in the ambient environment and/or emitted by other body organs in the vicinity of the transducer) from the desired signal in real time. Accomplishing this task will not only lead to greater accuracy in the measurement of physiologic sounds, but it will also allow the device to operate with a greater degree of autonomy when compared to analogous art.

Lastly, acoustic signals from human organs occur over many different frequency ranges (depending on the specific organ and any pathology present) and are often of minimal intensity. Therefore, detecting differences in these signals between normal physiologic and pathologic states over a finite time interval for any given organ requires a system of mathematical analysis with greater sensitivity than that described in many versions of analogous art. The device may provide a means for adjusting the frequency band in the Power Spectrum Density (PSD), which the RMS values are calculated from. The PSD results from performing the FFT on the digital data corresponding to the audio signal.

As noted above, this disclosure relates to a system for recording and analyzing physiologic sounds to provide the clinician with information relating to functional status of the organ being examined. This information may provide clues, that when combined with other elements of a diagnostic workup (history, physical exam, lab tests, medical imaging, etc.) may facilitate the diagnosis of various disease states (pulmonary disease for example). Consistent with other forms of analogous art, the system includes a plurality of transducers, such as microphones embedded in small rubber tubes coupled to a thin plastic diaphragm(s) which may be placed at pre-selected sites on the patient using either light pressure or a harness of some type. Physiologic signals of interest vibrate the plastic diaphragm, which transmits the sound by moving air molecules in the tube. The transducers detect these sounds and convert them into electrical signals. The system contains a preamplifier that not only increases the intensity of the incoming electrical signal, but also polarizes the transducers with an electromotive force (preferably 48 Volts) applied equally to both inputs to the sensor with respect to ground (phantom power). In order to provide this polarizing potential high voltage commercial alternating current is converted to high voltage direct current. This voltage is applied to same wires that carry the audio signal. Since the preamplifier can supply such high voltage (unlike many computer sound cards available commercially) the apparatus and method disclosed can make use of transducers with higher signal to noise ratios than those used in analogous art. Furthermore, portability may be maximized by supplying the phantom power through a alkaline, lithium-ion or other rechargable battery.

The system also includes a digital signal processor for conditioning the signal (filtering, gating, limiting, or excluding background noise). In an embodiment of the invention, analogue circuitry or a digital signal processor employing Super Harvard Architecture (SHARC) can be added for additional filtering, expansion, compression or conversion of the processed signal back to sound energy thereby enabling the operator to hear the altered sound in real time. After processing, the analogue signals generated by the transducers are converted into digital data and transferred to a computer workstation. In order to increase the portability of this device, digital data may be transmitted to the workstation over wireless internet. A further advantage of utilizing a SHARC processor is that optimal settings for detecting sound from a variety of sources may be stored in memory for instantaneous recall by the operator. These aforementioned settings which are programmed into the SHARC processor may enable the claimed invention to acquire properties of sound transmission which are identical to a conventional acoustic stethoscope. This is important because acoustic stethoscopes remain popular in clinical settings due to the fact that a tremendous amount of research has already been done with them and the steadfast hesitancy among healthcare professionals to abandon their use of these devices.

The computer station includes a microprocessor, input/output circuitry, and random access memory for data storage, one or more input devices (such as a keyboard or mouse), a modular interface with many different graphical displays of incoming data, and one or more output devices (such as a printer, monitor or modem for transmission over the Internet).

Executing on the computer is an application program constructed from a set of modular elements synthesized using a graphical programming language. The application program collects the data and organizes it into discrete sections (blocks) before moving it through a series of modules. By clicking on any specific module with the mouse, the operator can set the sampling rate, block size and overlap. Furthermore, the operator may elect to further high/low pass filter the data digitally or apply a mathematical window analogous to FFT processing in order to minimize distortion of calculated results.

After breaking the signal into multiple blocks (which correspond to discrete time intervals) and then pre-processing these blocks, the program calculates the power spectrum density of the portion of the signal contained in each block using the FFT. After calculation the computer displays the results graphically as a plot of Intensity vs. Frequency. These results are updated continuously as the PSD is calculated anew for each incoming block and the results of the previous block are saved in memory.

As the PSD is calculated for each incoming block, the computer may exclude portions of the PSD that are outside the selected thresholds specified by the operator. This is possible because the program may contain a trigger, which enables the operator to exclude portions of the spectrum, which are not of interest with a simple mouse click. Once the PSD is determined, the program calculates the root mean square (RMS) value of the signal in the frequency band(s) chosen by the operator. The computer performs this calculation on each incoming block and displays the data as a list during the time of operation. This method is highly advantageous to the clinician since it takes a very complicated quantity (the PSD of each block that gives information about the power of all frequency components in the block) and converts it into a simple quantity (RMS), while still relaying the necessary information about the signal to the clinician. Secondly, by performing these calculations on each incoming block of the data, the properties of the signal outlined above can be analyzed as they vary over time. The clinician can then use this information about an organ's spectral characteristics to assess its degree of functionality in a quick, inexpensive, accurate and non-invasive manner. The analysis program illustrated can be used either as a stand alone application or in combination with a number of additional program elements which may include patient's electronic medical records. As a result, this system has the potential to dramatically improve efficiency in the healthcare system and clinical outcomes for patients.

FIG. 1 provides an overview of the sound recording and analysis system of the present invention. This system includes a transducer 1, such as an analogue condenser microphone, which can be placed at various sites around the patient to listen to sounds emitted by different organs. It should be understood that the system could be expanded to include additional transducers 1 if desired so that data from multiple sites can be collected concurrently. To isolate the sensors from external sounds (and thereby improve signal to noise), they may be embedded in the tubing/chest pieces of conventional stethoscopes. The transducer(s) 1 may be held against the surface of the patient with mechanical pressure applied by the operator, adhesive tape or suitable strapping to prevent movement during the data acquisition process.

Leads 2 extending from the sensors are balanced cables with XLR inputs 97 that connect to a signal conditioning station. A suitable signal conditioning circuit could be the Eurorack 1202, a sound mixer 3 made by Behringer. This station performs many important functions. First, it supplies the electromotive force needed to polarize the transducer 1. In the preferred embodiment, the mixer 3 converts standard alternating current (120 volts) into direct current (48 volts). It has been proven that to accurately record physiologic sounds, it is important to have a transducer 1 with a high signal to noise ratio and a flat frequency response. These types of sensors may demand high voltages, which are not readily supplied by analogous art that utilizes sound cards built into most commercially available personal computers 9 or batteries.

The voltage is then supplied to the sensor through both XLR inputs 97 equally with respect to ground (phantom power) 93. The audio signal is transmitted through these same inputs approximately 180 degrees out of phase of each other thereby ensuring a balanced signal. Balanced signals are less corrupted by ambient noise relative to unbalanced ones. Inside the stethoscope tube, sound energy generated from organs inside the body is converted into an electrical signal by the microphone. This electrical signal (which is a representation of the sound) is then transmitted to the mixer 3 though the same leads 2 that supply the voltage in the manner described previously. To further prevent this desired signal from being corrupted by external electric/magnetic fields, the cables may be shielded. The mixer 3 may have additional ports to receive electrical signal from additional sensors. In addition, phantom power 93 may be supplied via alkaline (such as the ART Phantom Power Adapter), lithium-ion or other rechargeable 9 volt batteries.

Figure 3A:
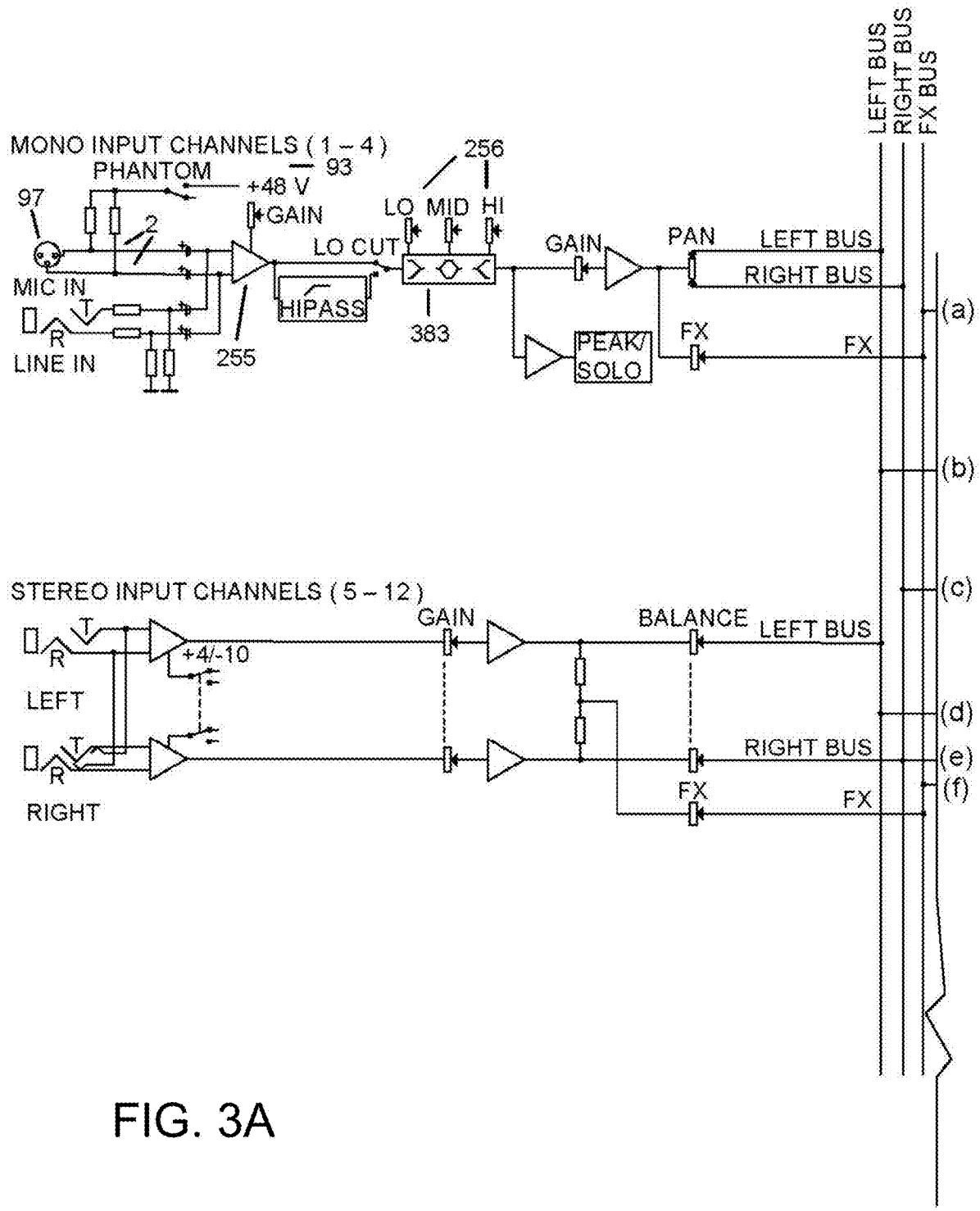
FIG. 3A illustrates a block diagram of an embodiment of the signal conditioning station.
Figure 3A:
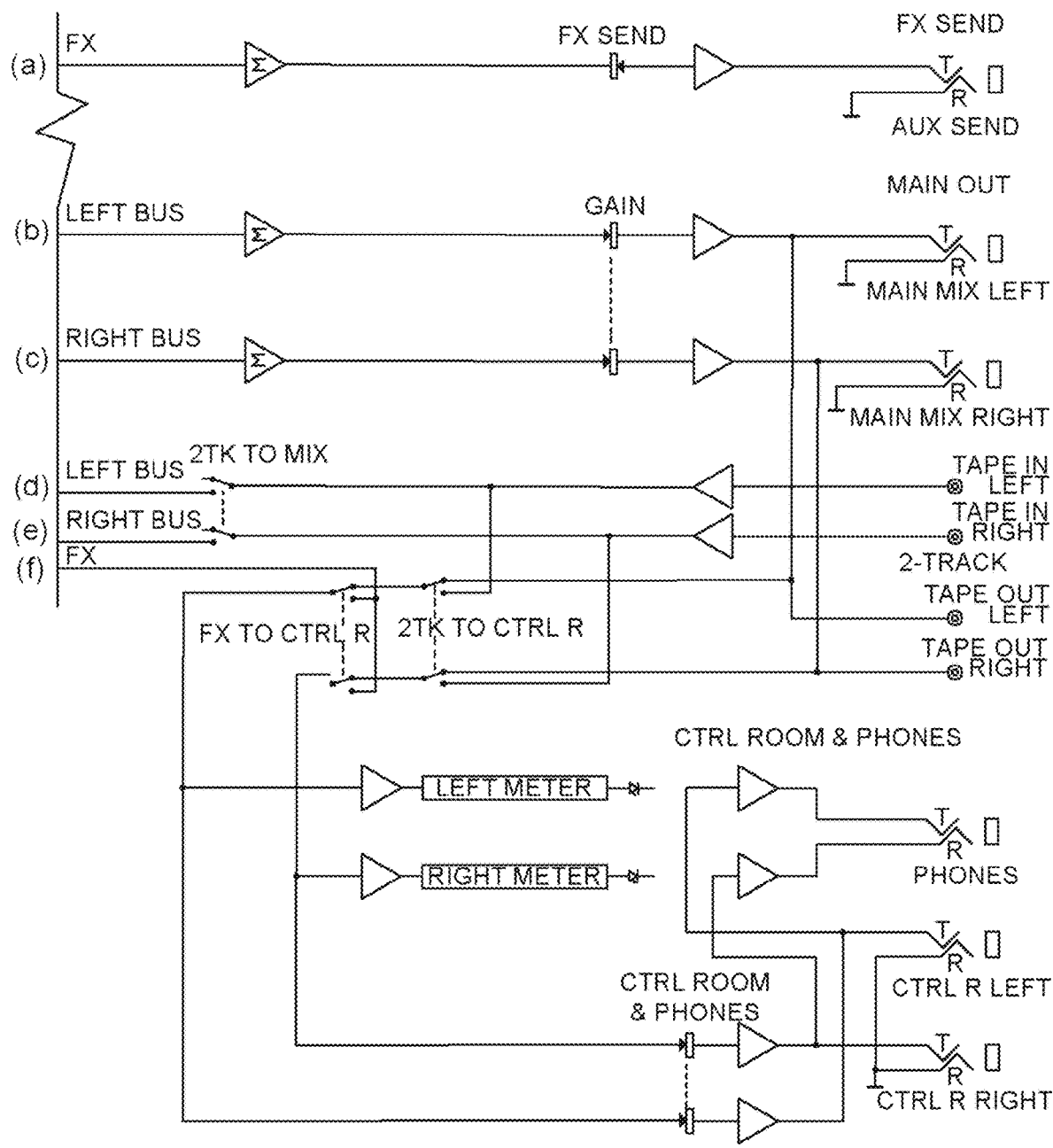
Figure 3B:
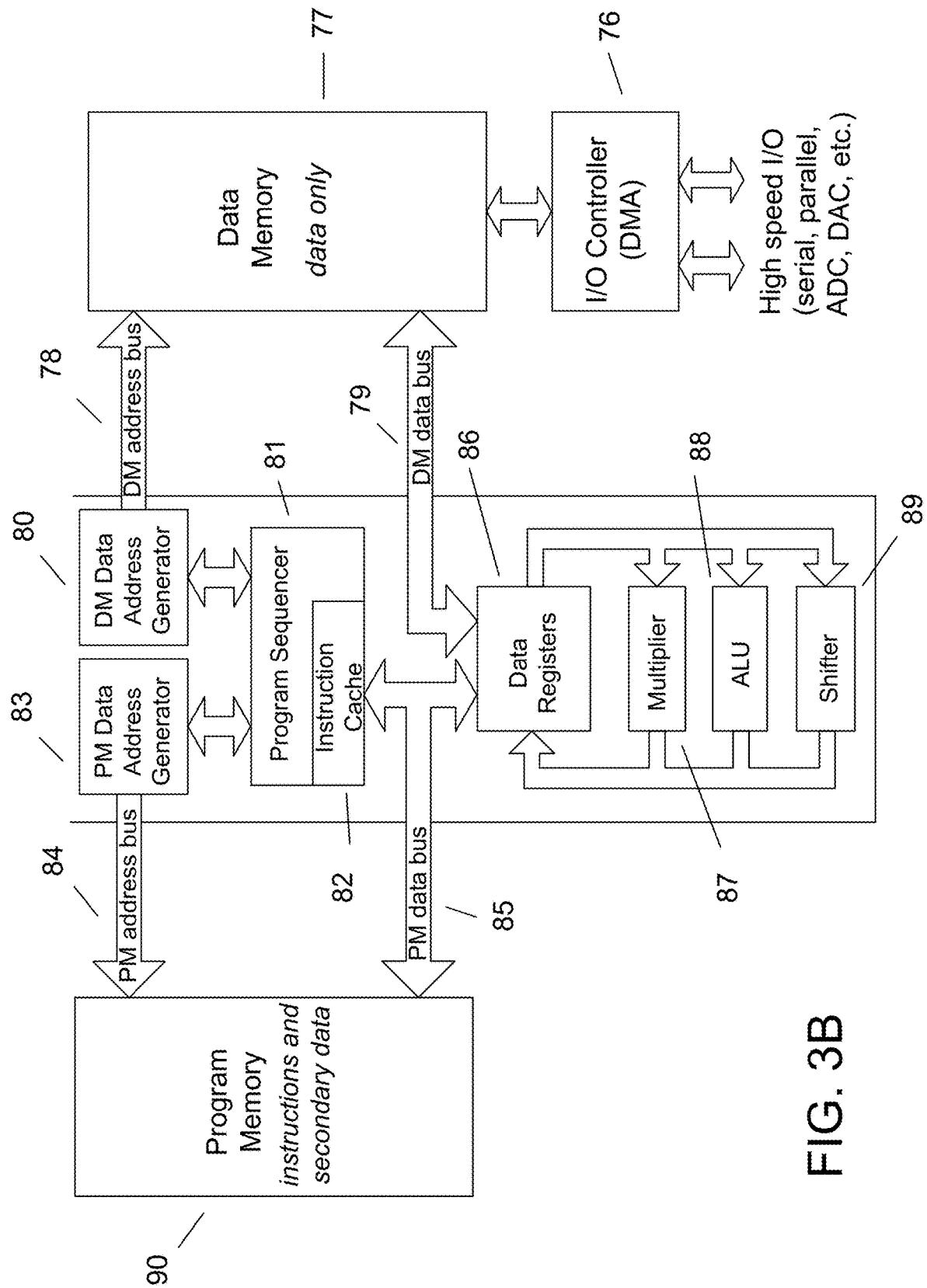
FIG. 3B illustrates a block diagram of the digital signal processor described.

Once the electrical signal is received by the mixer 3, it may be amplified 255 and/or filtered 256. In the preferred embodiment the mixer contains circuitry 383, which can act as a high pass filter (80 Hz) 256 and/or low pass filter (12 kHz) 256, although other frequencies are possible. It should be noted that the invention gives the operator the ability to bypass this processing if they choose. After amplification/filtering, the signal may be sent to a headset 4 where it is converted back to sound energy, thereby enabling the operator to listen to the sound as it is recorded. The signal may also be sent for recording on cassette tapes or it can be sent to a digital signal processor (DSP) 5. One such example is the DEQ 2496, a digital equalizer with Super Harvard Architecture (SHARC) signal processors 76,77,78,79,80,81, 82,83,84,85,86,87,88,89,90 and specialized software, made by Behringer which is depicted in FIGS. 3A and 3B.

The digital processor 5 performs the fast Fourier transformation on the signal and displays both the discrete frequency bands and the power of the signal in each band (power spectrum density) 621, as shown in FIGS. 8 and 10, for example. One of ordinary skill in the art will understand that the waveforms shown in FIGS. 8 and 10 (as well as other waveforms, such as FIG. 12A) are merely exemplary, and that the ordinate or Y-axis demonstrates relative values, such as decibel (dB) shown, as well as other measures of PSD, such as, but not limited to, RMS. From here, the operator can selectively amplify/attenuate components of the signal in any frequency band from 20-20000 Hz (similar to an equalizer) 612-615. Unwanted signal can be excluded by compressing 615 (the processor reduces the intensity of all signal components with a volume that is greater than desired) or expanding 615 (reducing the intensity of all frequency components with an intensity less than that desired by the operator) frequencies detected by the transducer 1. Of note, the device can function as a noise gate and/or limiter if compression/expansion is performed to a maximum degree. All operations undertaken by the digital signal processor 5 to alter the incoming audio signal can be displayed via LCD, and device operations 612-620 and 622-623 may be saved in memory by device operation 620 for instant recall by the operator at some future time. The adjustment of stereo width function 623 may or may not be necessary. It is understood that specific operations 612-619 of the digital signal processor 5 may cause the invention to acquire properties of sound transmission similar to conventional acoustic stethoscopes. This characteristic of the claimed invention is a valuable attribute, since a tremendous body of research has already been conducted in the analysis of physiologic auditory signals using said acoustic stethoscopes. Secondly, it is well known that such conventional stethoscopes are still widely popular in the market place. Specifically, settings contained in the digital signal processor 5 may allow clinicians to measure blood pressure values, grade cardiac murmurs (I-VI) and listen to other physiological sounds in a manner which correlates well with findings obtained from a conventional acoustic stethoscope. The ability to perform compression/expansion is an improvement over other forms of analogous art since it allows the device to record physiologic sounds from the human body without having to constantly be directed to by the operator. However, it should be noted that the device might set up so that it is required to be directed by the operator before making recordings.

Furthermore, the digital signal processor 5 contains a test transducer 1, which can be deployed by the operator if desired. This test transducer 1 may be affixed to body surface or exposed to the ambient environment. The test transducer 1 records sounds from sources that might corrupt the signal being recorded from the organ of interest. This may include noise present in the ambient environment or sound emitted from other organs in the vicinity of the target organ. The power spectrum density 621 of these ambient signals can be used to calculate and display 622A the corresponding RMS values for the signal as demonstrated in FIG. 5. The components of the undesired signal, which interfere with the signal of interest, are effectively quantified in real time. The DSP 5 may transmit data directly to a computer workstation 9 for further analysis via cable or wireless internet connection 16, 17. This is a significant improvement over analogous art because it can be used to remove ambient noise that contains identical frequency components to those of the target organ, thus producing a much clearer signal from the target organ in addition to enabling the clinician to obtain standardized measurements regardless of the noise level present in the ambient environment at the time of measurement. The processing methods may include (but is not limited to) graphic 612, parametric 613, digital 614 and/or dynamic equalizers 615, as well as signal compression/expansion/boosting/cutting and feedback destruction 622 or bypassed altogether 616.

After this additional processing, the signal from each analogue output is transmitted to an analog-to-digital converter (A/D converter) 6, which may or may not be part of the computer station 9. The A/D converter 6 converts the processed audio information into a digital data stream for transmission to the workstation 9. One advantage of employing a SHARC processor 5 is that digital data may be transmitted to the computer workstation 9 over wireless internet 16,17. This process can be achieved by coupling the SHARC processor 5 to a modem 16 with a WiFi PC card (not shown). Digital data acquired during stethoscope operation may be transferred to a WiFi Access Point/Router 17, and afterward, sent to a modem 16 via CATS cable or WiFi USB adapter.

Figure 3C:
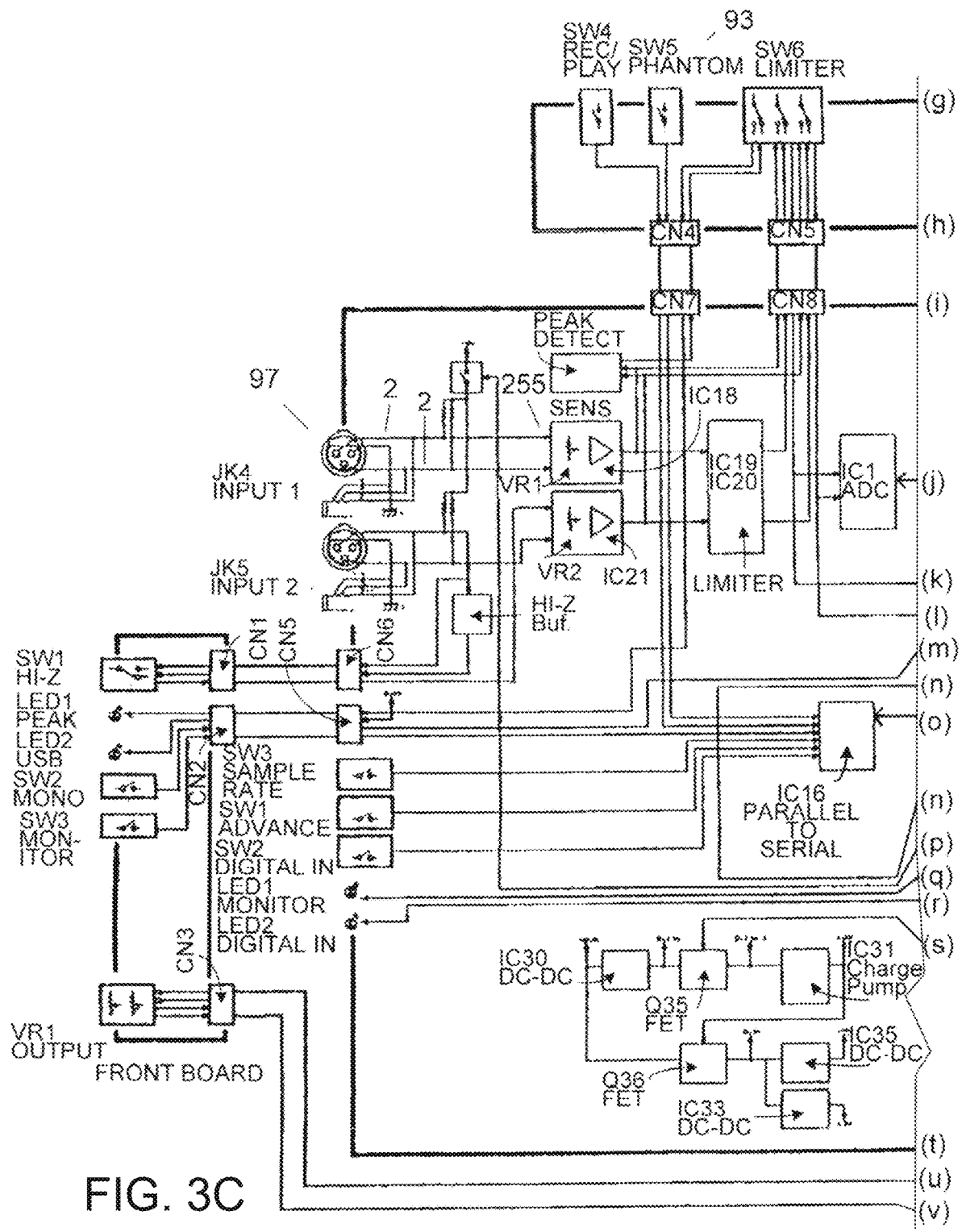
FIG. 3C is a block diagram of elements utilized in data conversion and transfer incorporated within an embodiment.
Figure 3C:
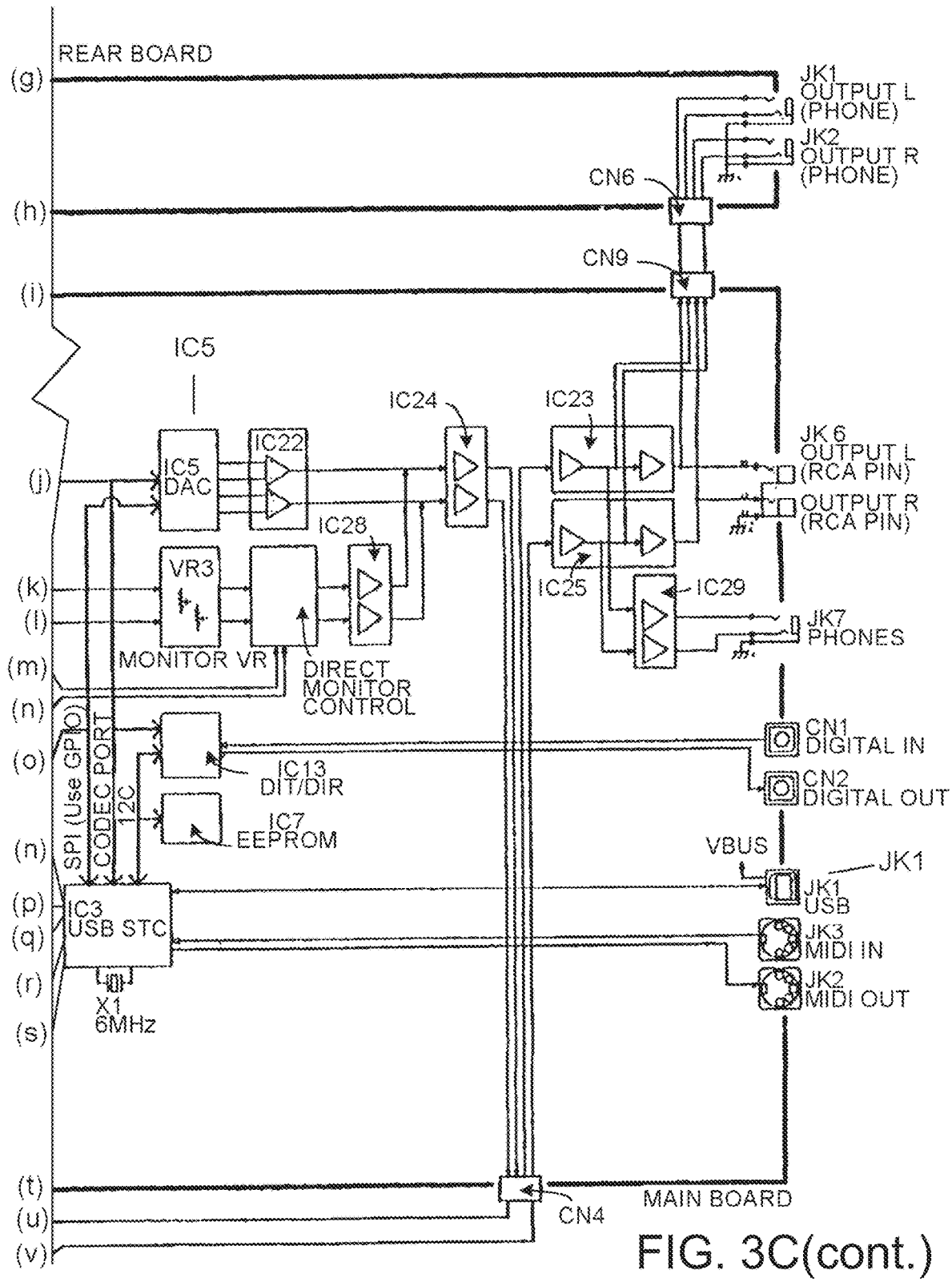
Figure 4D:
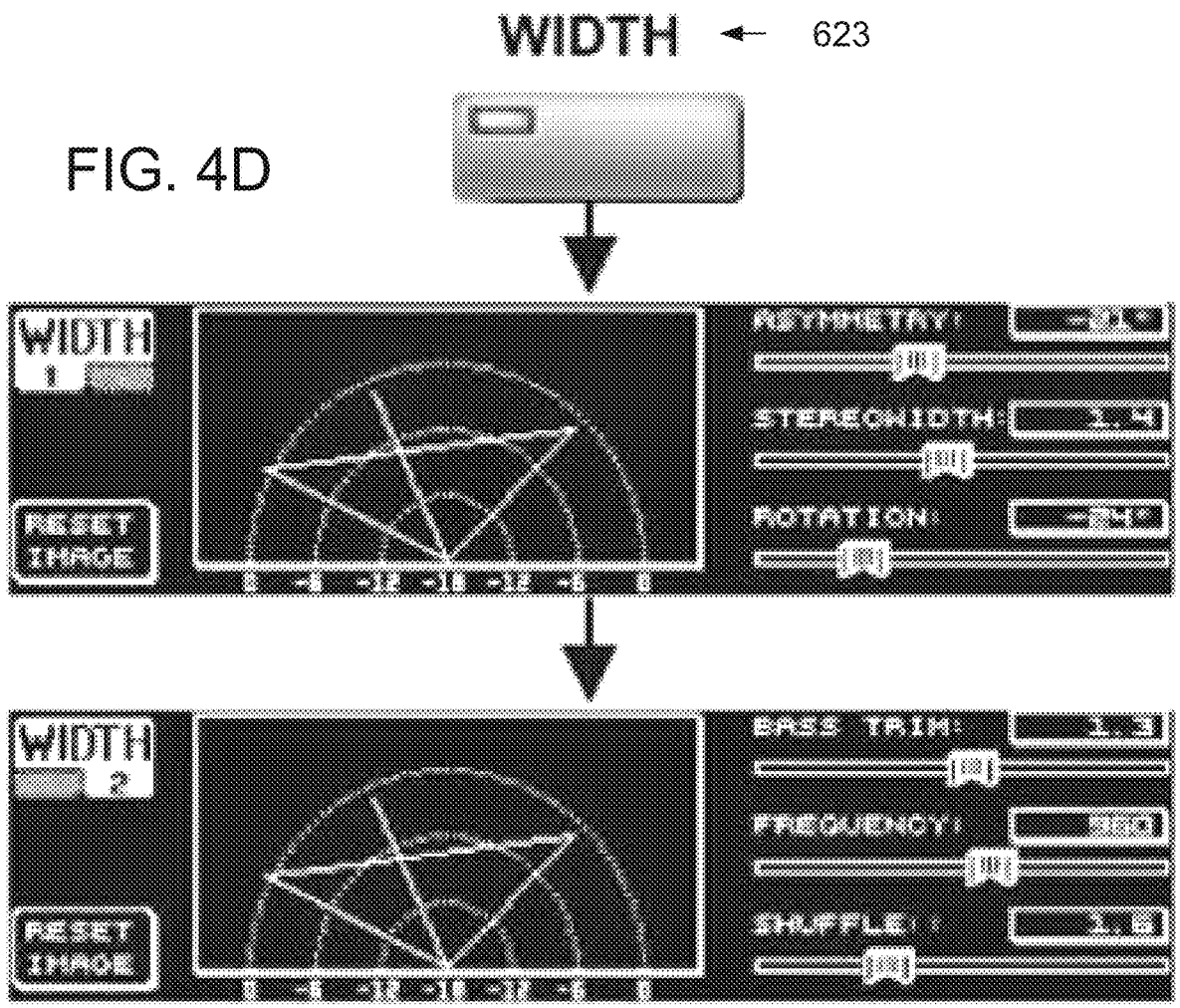
Figure 4G:
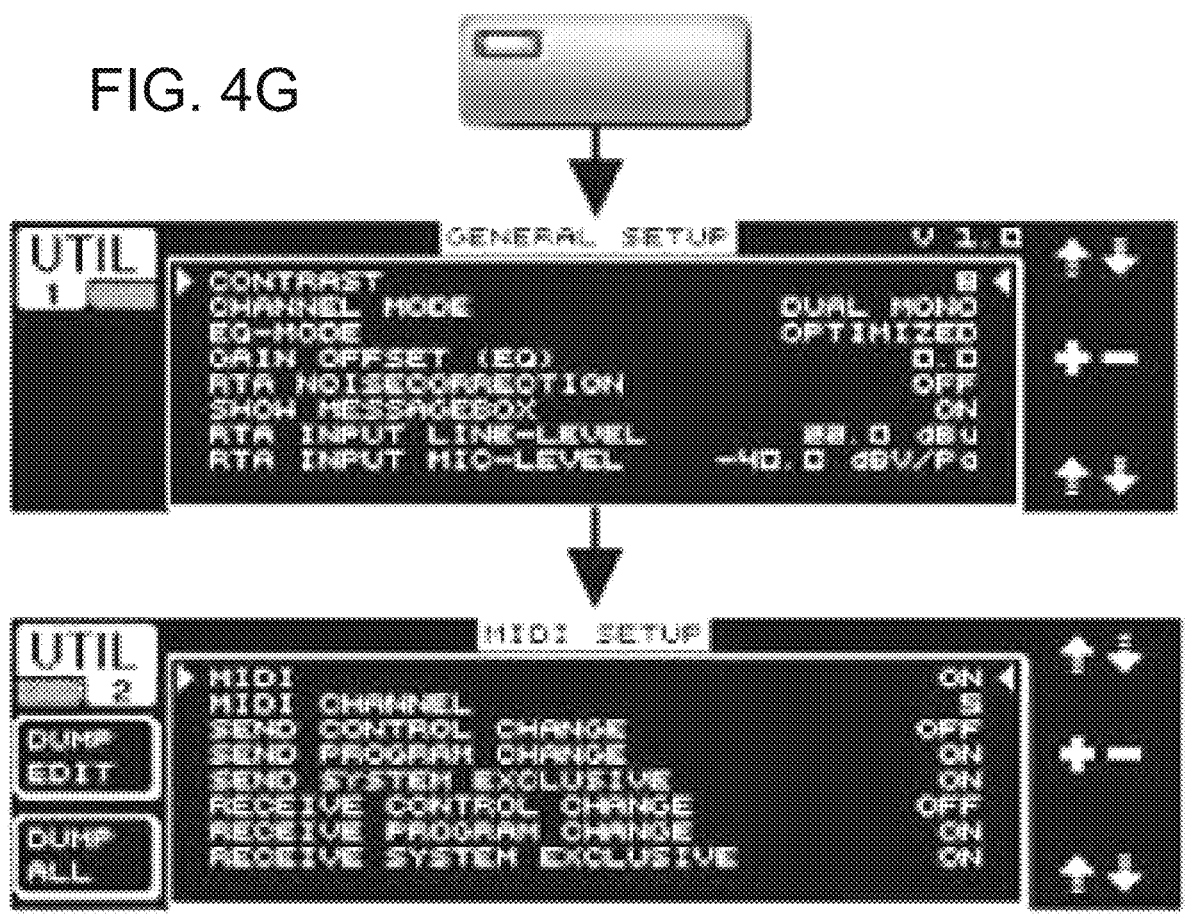
Figure 4H:
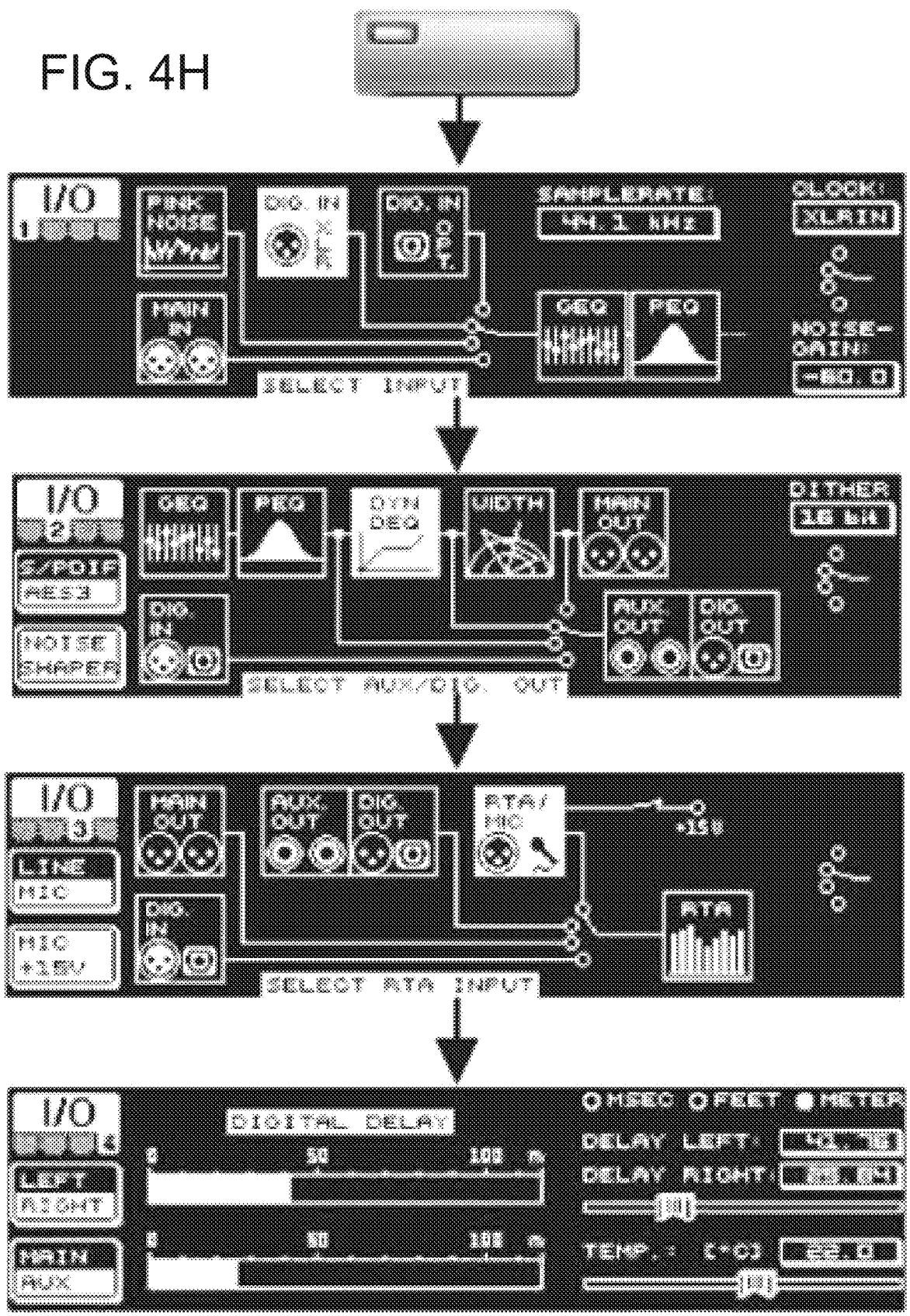
Figure 4I:
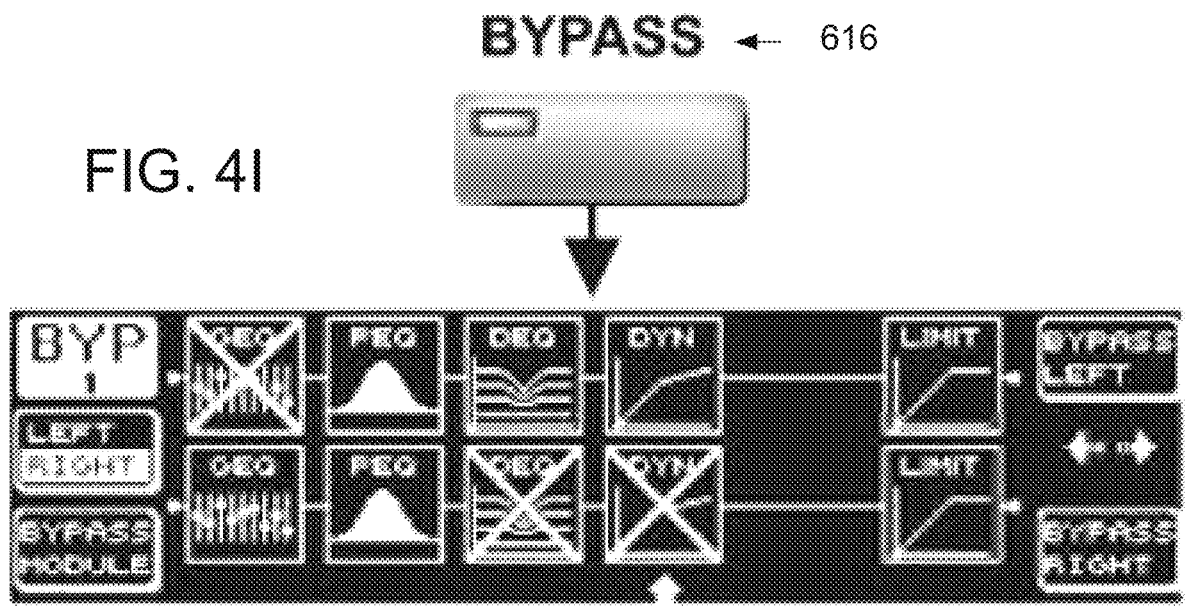
Figure 4J:
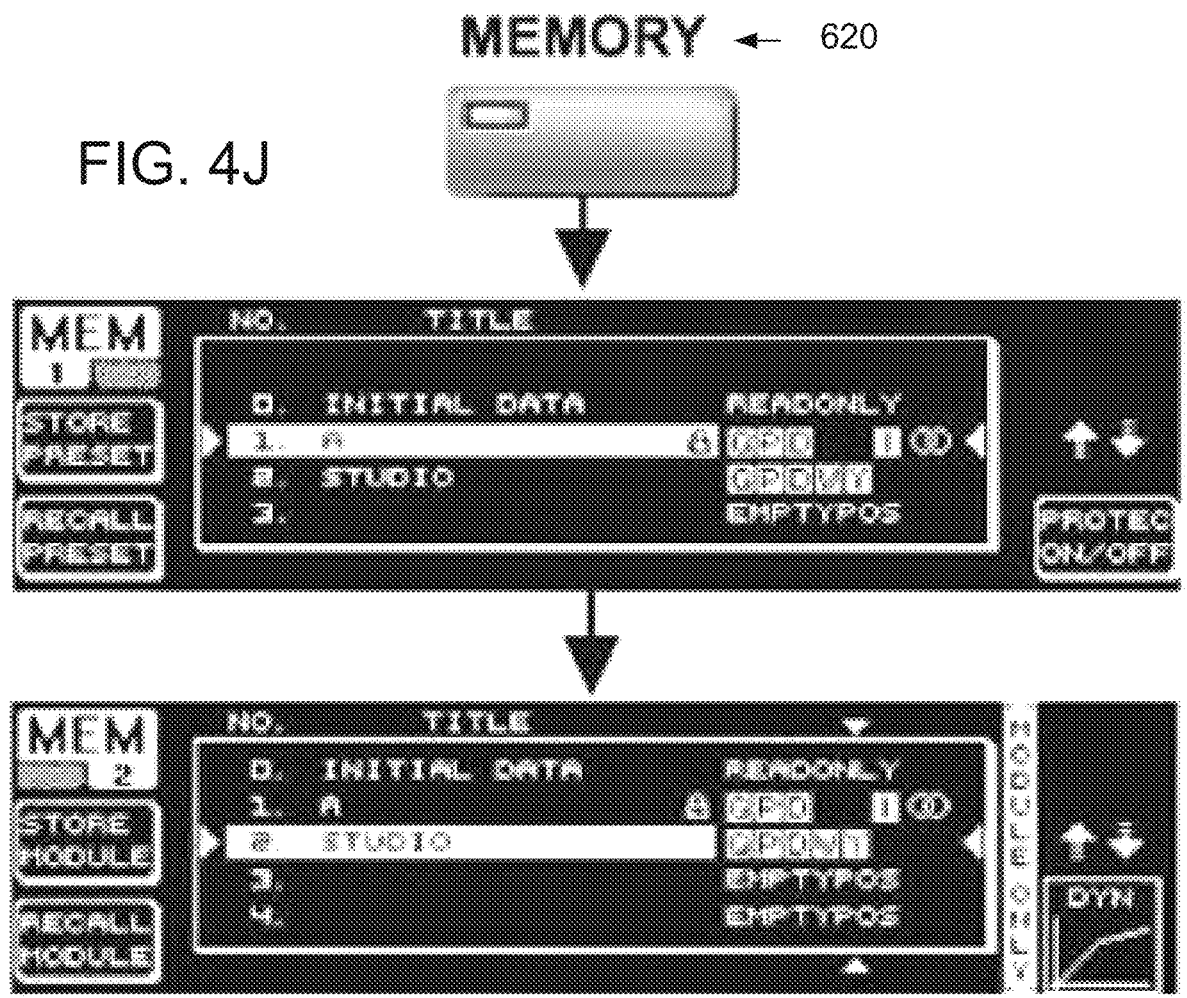
Figure 4K:
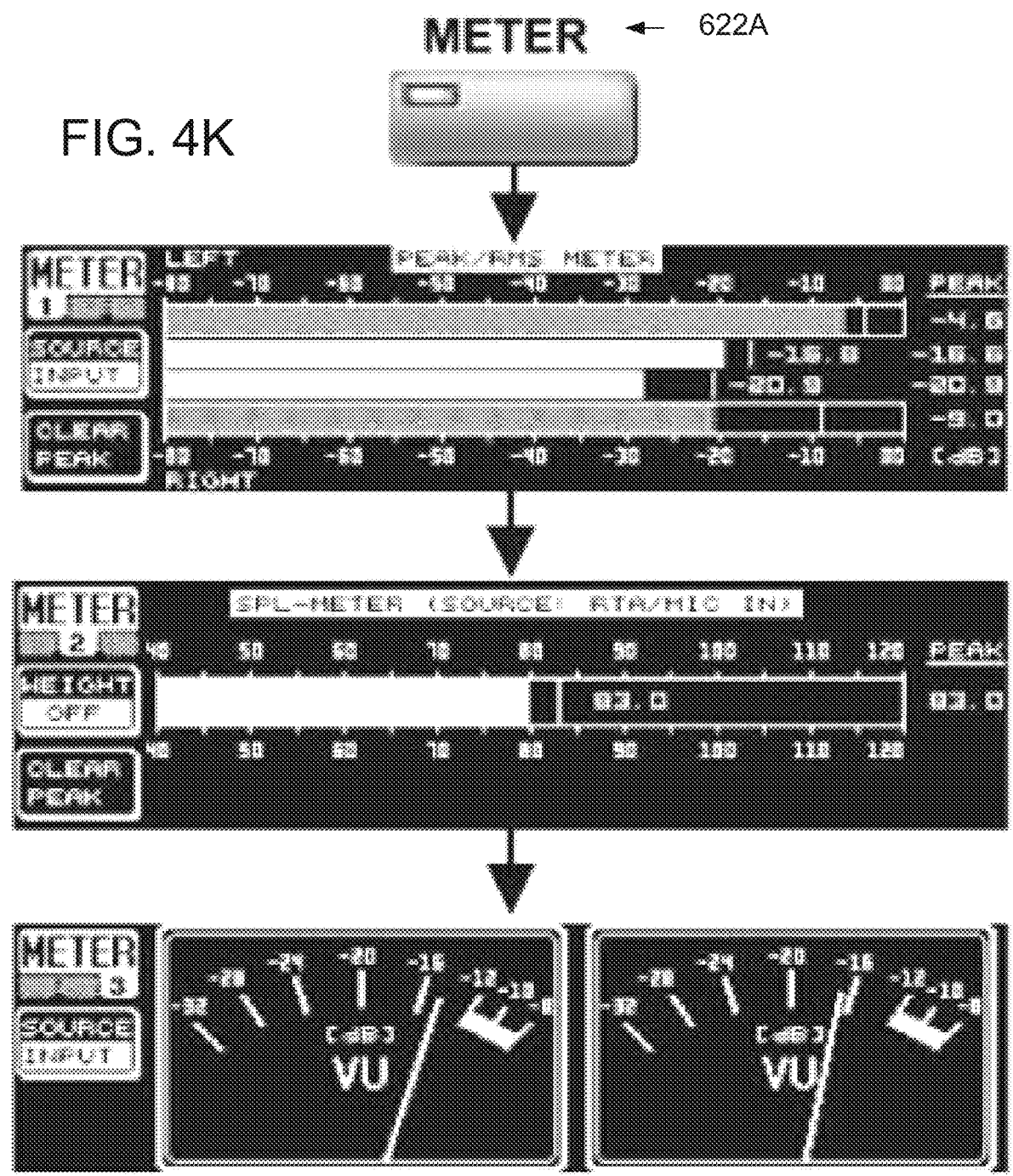
Figure 4L:
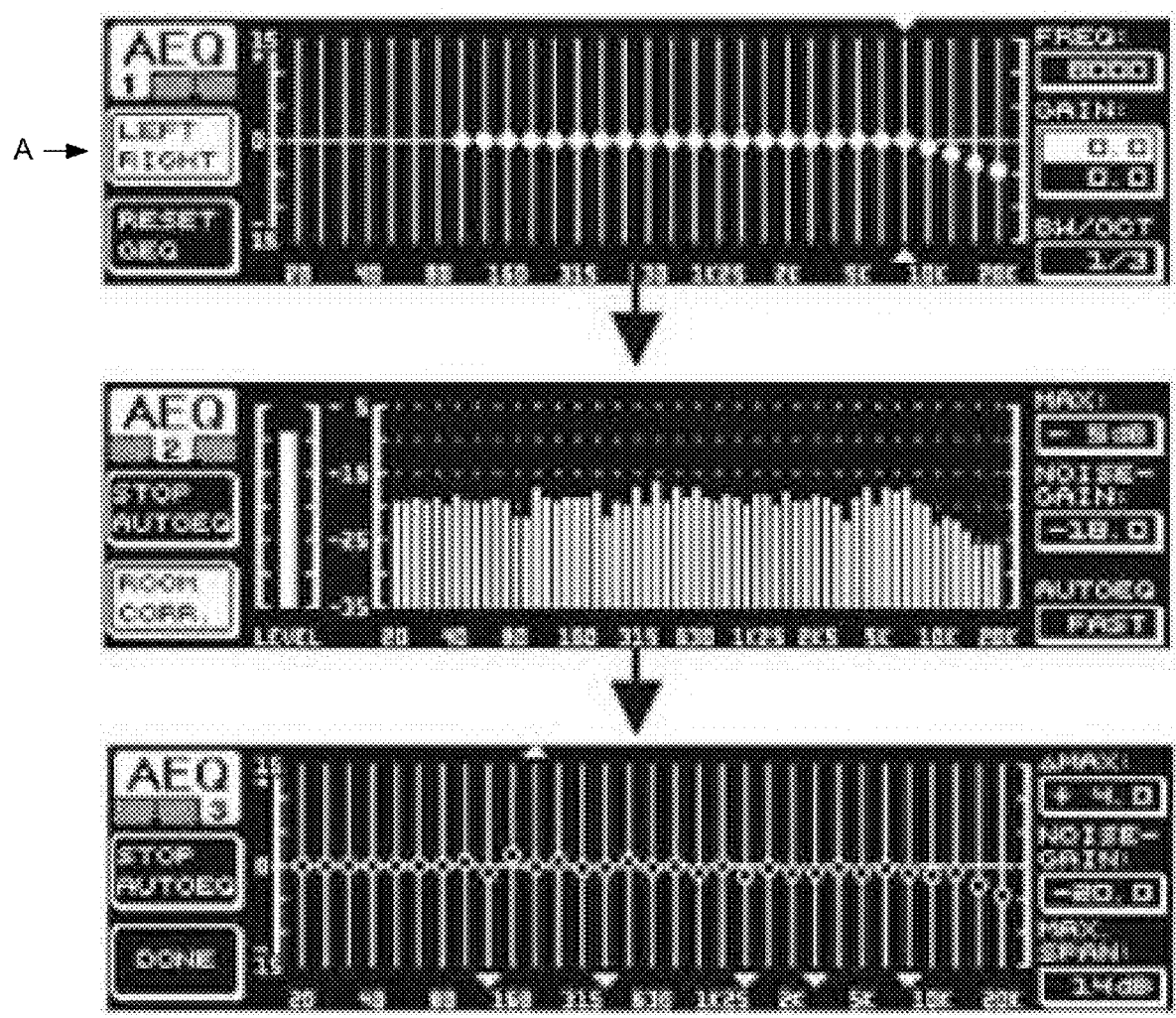
Figure 6:
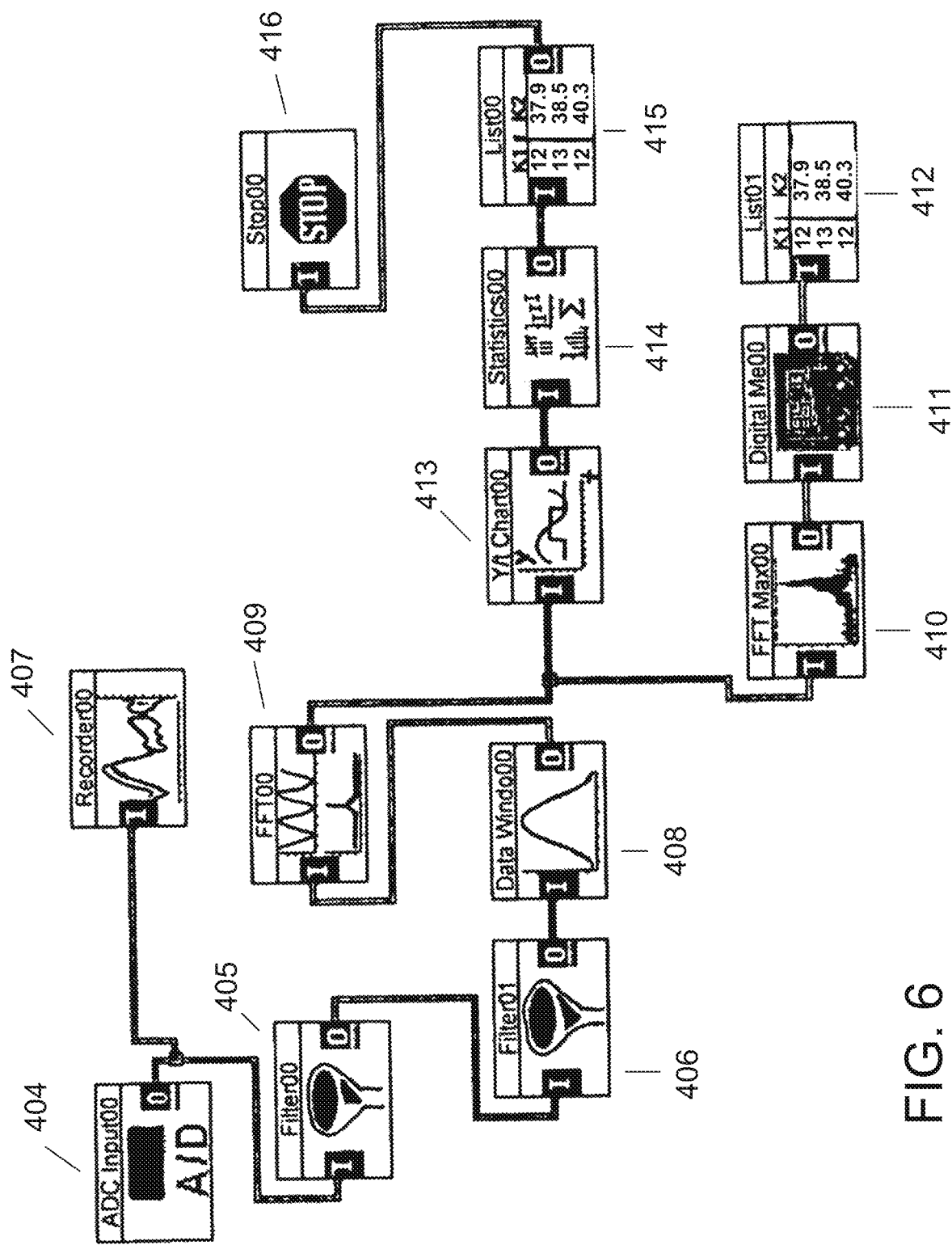
FIG. 6 is a flow chart of the data collection and analysis program. Each icon represents an operation which is performed on incoming data and selecting a corresponding icon can modify these operations.

The sampling rate used in digitizing the data may be adjusted by the operator and should be greater than 44.1 KHz with a bit rate preferably greater than 24 bits per sample. The A/D converter 6 is preferably multi-channel which may contain an additional preamp such as the Edirol UA-25 sold by the Roland Corporation. FIG. 3 is a schematic of all of the hardware components which comprise the preferred embodiment of the invention (components for transmission of data over a wireless network are not shown). FIG. 3A illustrates a first portion of a first schematic connected to a second portion of the first schematic, illustrated in FIG. 3A (cont.), through lines (a)-(f). FIG. 3C illustrates a first portion of a third schematic connected to a second portion of the third schematic, illustrated in FIG. 3C (cont.), through lines (g)-(v). A suitable workstation 9 may be a personal computer of the E-machines series as sold by Lenovo, comprising a microprocessor 12, input/output circuitry 10, and memory for data storage 13, one or more input devices (such as a keyboard 8 or mouse 7), a modular interface with many different graphical displays of incoming data as depicted in FIG. 6, and one or more output devices such as a printer 15, monitor 14 or modem 16 for transmission over the Internet. As shown in FIG. 1, input/output circuitry 10, microprocessor 12, and memory for data storage 13 are interconnected via bus 11. However, it should be understood that other models may be substituted. These computers are controlled and coordinated by operating system 16A, such as Microsoft Windows XP or other system. The operating system 16A may also comprise a window manager 17A, printer manager 18 and additional device managers 21 in addition to one or more device drivers 19,20,22 in order to allow the computer workstation 9 to interface with hardware components.

Figure 2:
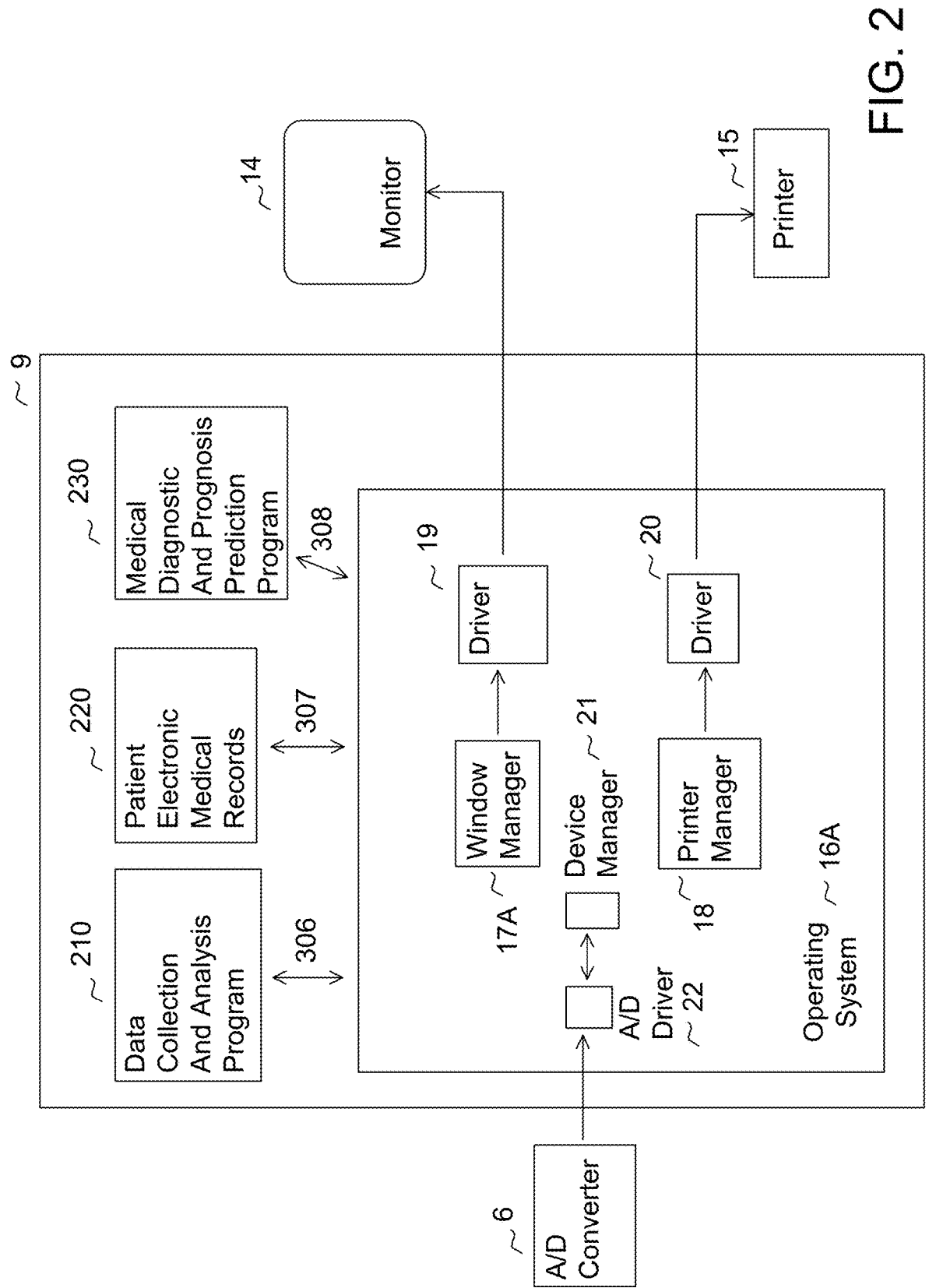
FIG. 2 is an illustration of the computer station component of FIG. 1.

Digital data from the A/D converter 6 is transmitted to input/output (I/O) circuitry 10 of the computer via USB cable JK1. FIG. 2 illustrates the interaction of software elements on the computer workstation 9 with the application programs 210,220,230 and operating system 16A relationships shown by arrows 306,307,308 via system calls. The program (FIG. 6) is organized by a series of graphical icons that are provided via specialized data acquisition software such as DASYLAB 9.0, a product manufactured and sold by Capital Equipment. Each icon, constructed using a graphical programming language, represents a command(s) for the workstation 9 to perform. This program 210 is fully customizable since simply inserting/deleting icons in the flow diagram can make new programs. All commands given to the analysis program by the clinician are accomplished via simple keyboard 8 entries or mouse 7 "clicks". Thus, knowledge of computer programming languages (which many health care personnel do not possess) is not a required prerequisite for proper operation of the instant device.

Figure 7A:
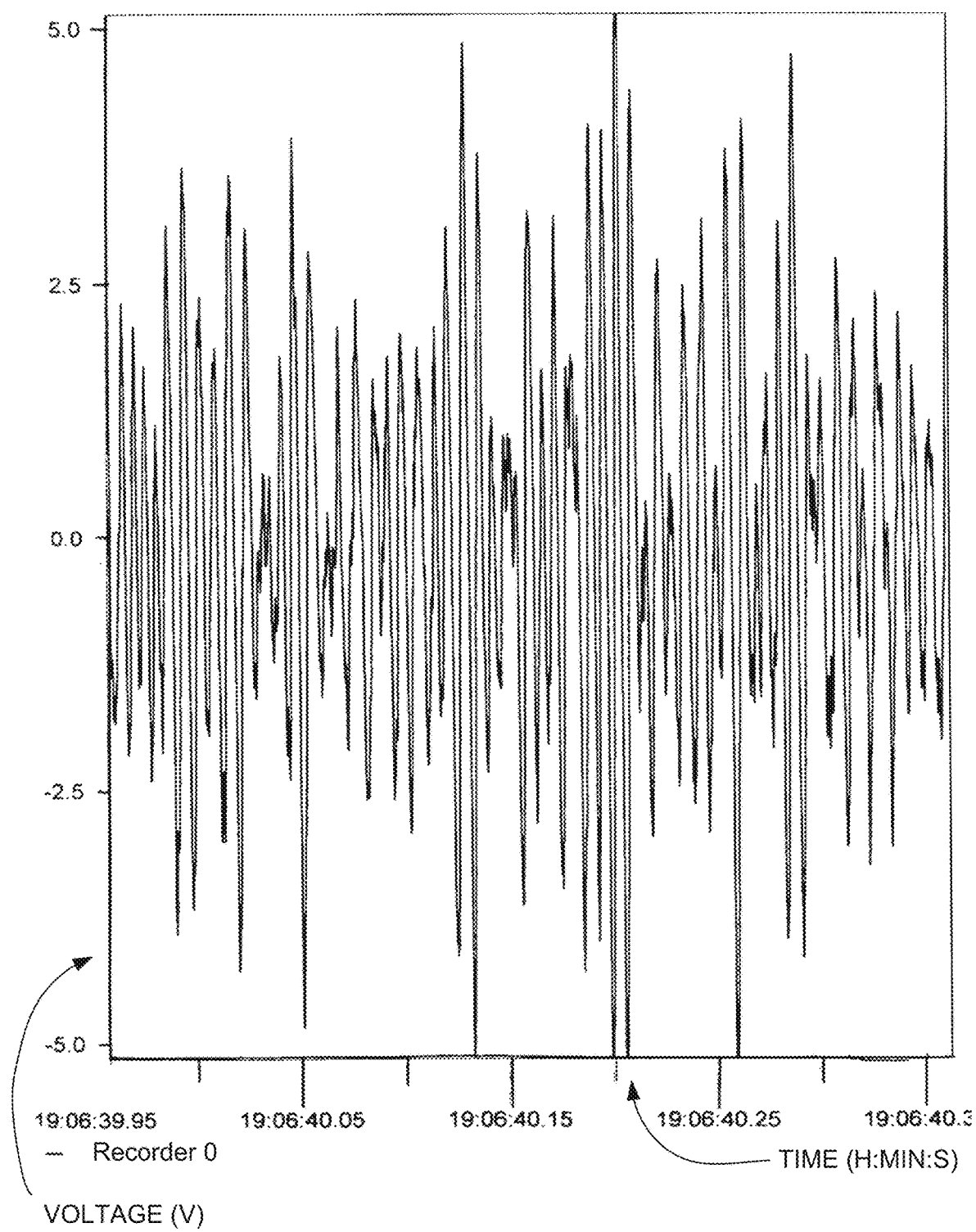
Figure 12A:
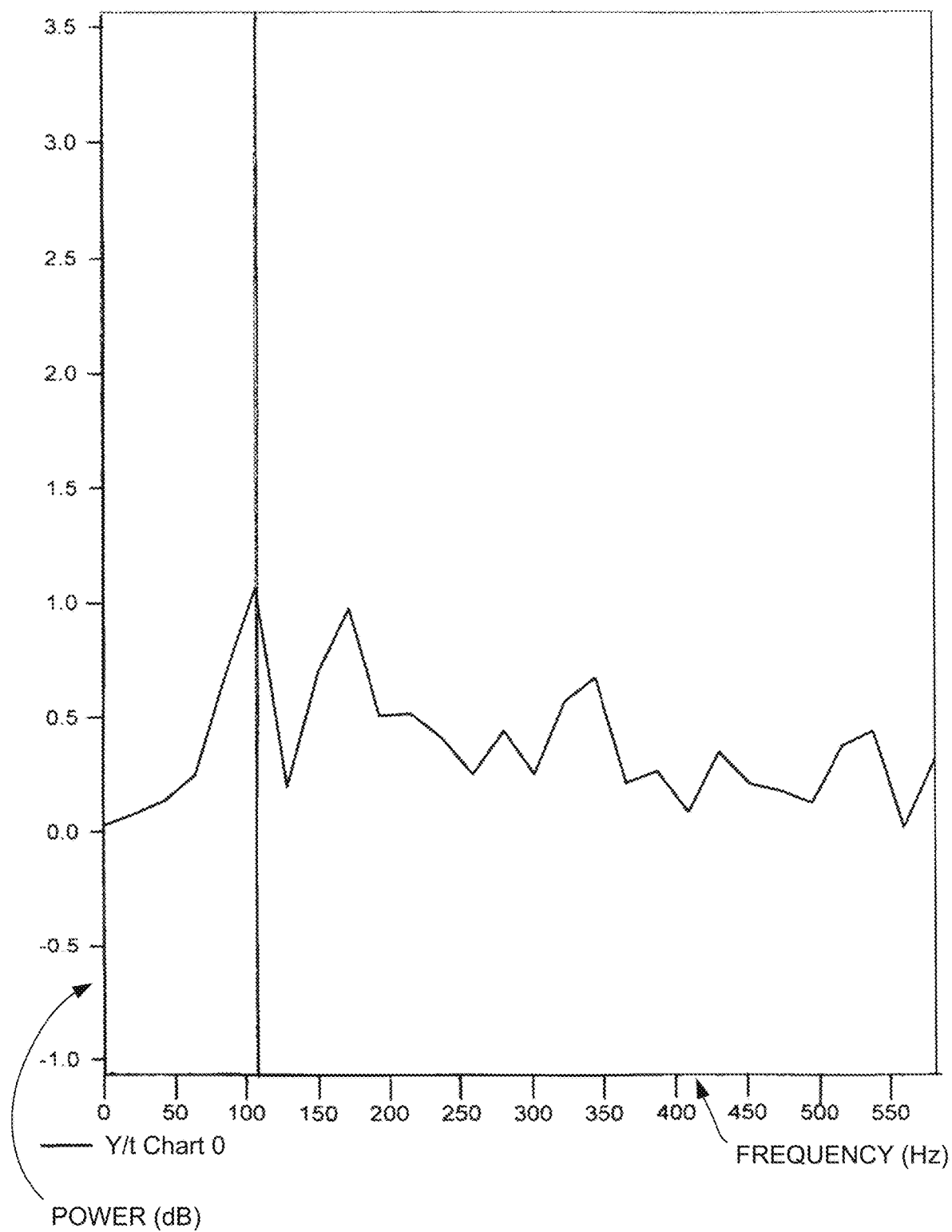

Prior to first listening to the sound the clinician chooses the sampling rate by clicking on a tab marked "experimental setup." The A/D input icon 404 receives data via I/O circuitry 10. The Recorder Icon 407 displays the time-expanded function of the incoming signal illustrated in FIGS. 7A and 7B in accordance with the description set forth in U.S. Pat. No. 3,990,435. The clinician then clicks the Filter icons 405,406 in order to select frequencies where the signal can be high/low pass filtered digitally. Some examples include digital high/low pass filtering, application of a windowing function to incoming data analogous to PSD calculation, adjustment of sample rate, block size, degree of overlap and recording time. Through the use of these icons, the clinician may also determine the characteristic (Butterworth, Bessel, etc.) and order of the digital filter. The clinician will click the Data Window Icon 408, to select the desired block length, appropriate mathematical window to fit the data with, and determine the degree of overlap (if any) between successive blocks. The FFT icon 409 in the program 210 instructs the computer to calculate the FFT on the portion of the signal represented by each block. The Y/T Icon 413 enables the clinician to view a display of the PSD on a monitor 14 for each block after it is calculated as illustrated in FIGS. 8 and 10. By clicking the FFT max icon 410, the clinician can specify the frequency range within the PSD where both the frequency of maximum intensity and its magnitude may be calculated as illustrated in FIGS. 12A, 12B and 12C. These quantities may be displayed by the icon marked "Digital Meter" 411 or List icon 412. By clicking the Trigger Icon, the clinician can determine which frequency components of the PSD will be excluded from the RMS calculation (not shown).

Since different body organs emit sound in different frequency ranges, the ability to adjust the frequency range is vital if one hopes to construct a single device that can be used to analyze sounds from all of the different organs (not just lung). The Statistics Icon 414 instructs the computer to calculate the RMS value of the signal in the desired frequency range set by the digital high/low pass filters 405,406 or Trigger Icon in the specified range. The List Icon 415 displays the RMS value sequentially as it is calculated from each incoming block as shown in FIGS. 10 and 12. Additional modules may be added to the program 210 for the purpose of determining the magnitude of the change in RMS values with respect to time at a given anatomic position. These RMS values, either as displayed by the List Icon 415 or when combined with additional analysis programs 220, 230 on the workstation 9, give the attending physician a mechanism for comparing the intensity of physiologic sound recorded by the sensor in any desired frequency range and over any duration of time.

In operation, the sensors 1 are affixed to any part of the body surface according to the discretion of the clinician. The system is then initialized and data is transmitted to application program 210, as the patient inhales/exhales, sound is converted to audio signals which may be amplified/filtered/processed before being relayed to both the clinician and the application program 210 in the computer workstation 9. At any instant in time (if the physician hears an interesting sound) the physician can start the digital recording by clicking the Recorder Icon 407, a green arrow in the upper left hand corner of the screen. After the signal of interest is no longer audible, the physician may stop recording by clicking the red square icon or specifying the duration of recording via the "Stop" icon 416. The computer recording may be influenced by the DSP 5 via compression/limiting 615 or equalization 612,613,614 as described above. After recording is complete, the clinician may click the list icon 415 to obtain a columnar display of the desired RMS values. Review of this list may give the clinician valuable information regarding the degree of functionality/pathology present in certain organs (lung, heart, bowel, etc.). The settings and/or outputs of the PSD (calculated from the Y/T icon 413), Time Expanded Waveform 407, FFT Maximum 410, Filters 405,406 and List 412,415 can all be saved in memory 13, printed on paper via printer 15 or transmitted via modem 16 to another computer 9 though the internet. It should be understood that additional icons may be added to the program in FIG. 6 if additional data manipulation is desired. In addition, program settings for analysis of auditory signals from two or more different sources (organs, ambient noise, etc.) such as the heart and trachea (FIGS. 9 and 11) may be combined, thereby enabling the operator to analyze discrete frequency bands within a signal. For instance, if an observed physiologic sound is composed of sounds from the trachea and heart superimposed on each other, the operator may combine modules from FIGS. 9 and 11 into a single program that will separately analyze the signals from each source simultaneously. If there exists overlap, additional methods may be deployed to separate out the overlapping frequency components of the two or more sources.

Lastly, data generated from this analysis program 210 may be integrated with numerical/text data contained in a patient's electronic medical records 220. The integration of data among these programs 210,220,230 can be directed by an operator using a mouse 7, keyboard 8 or other input. U.S. Pat. Nos. 6,944,821 and 6,154,756 demonstrate two such methods for performing said integration of data contained on multiple program elements. Additional software programs 230 may combine data from the analysis program 210 and electronic medical records 220 for the purposes of assessing target organ functionality, characterization of pathology if present, and generating accurate predictions regarding the degree of functionality of the target organ system in the near future.

It is to be understood that even though numerous characteristics and advantages of various embodiments of the present invention have been set forth in the foregoing description, together with details of the structure and function of various embodiments of the invention, this detailed description is illustrative only, and changes may be made in detail, especially in matters of structure and arrangements of parts within the principles of the present invention to the full extent indicated by the broad general meaning of the terms in which the appended claims are expressed.

What is claimed is:

1. An apparatus for acquiring and processing physiological sounds comprising:
   a sensor configured to convert an analogue signal into an electrical output representative of a first physiological sound;
   an analogue to digital converter operatively coupled to said sensor, wherein said analogue to digital converter is configured to convert said electrical output into a stream of digital data; and
   a display device configured to display a plurality of icons, wherein said plurality of icons displayed on said display device is configured for customization by a user through insertion of an additional icon in said plurality of icons displayed, and wherein the apparatus is configured to initiate a recording, by interaction of said user with at least one icon in said plurality of icons displayed, of a signal representative of a second physiological sound that is received over a network.

2. The apparatus of claim 1, further comprising:
   a serial to parallel converter operatively coupled to said analogue to digital converter, said serial to parallel converter configured to convert at least a portion of the stream of digital data into a parallel output.

3. The apparatus of claim 2, further comprising:
   a digital to analogue converter operatively coupled to the serial to parallel converter, said digital to analogue converter configured to convert at least a portion of the parallel output into a second analogue signal for transmission over the network, wherein the network is a wireless network.

4. The apparatus of claim 2, said apparatus further comprising: a processing unit operatively coupled to said serial to parallel converter, said processing unit configured to compute a mathematical transform on at least a portion of said parallel output.

5. The apparatus of claim 1, wherein said display device is configured to display information comprising a vital sign.

6. The apparatus of claim 1, wherein said physiological sounds are sounds generated by an organ in a frequency range up to 20,000 Hz, and wherein said sensor is one sensor of a plurality of sensors and at least two sensors of said plurality of sensors are configured to convert said physiological sounds into a plurality of corresponding electrical signals.

7. The apparatus of claim 6, wherein said plurality of sensors comprises at least three sensors.

8. The apparatus of claim 2, wherein said apparatus is characterized as a first apparatus, and further comprising a second apparatus operatively coupled to said first apparatus, said second apparatus further comprising:
   an electronic memory configured to store a signal representative of at least a portion of said parallel output; and
   a processing unit coupled to said electronic memory, said processing unit configured to retrieve from said electronic memory and process said signal representative of at least a portion of said parallel output into a processed signal.

9. The apparatus of claim 1, wherein the physiological sounds are ambient noise generated by an organ in a frequency range up to 20,000 Hz.

10. The apparatus of claim 6, wherein at least one sensor of said plurality of sensors is configured to be positioned on a body surface.

11. The apparatus of claim 7, wherein at least one sensor of said at least three sensors is configured to be positioned on a body surface and wherein said physiological sounds are sounds generated by an organ in a frequency range up to 20,000 Hz.

12. The apparatus of claim 10, wherein said display device is configured to display information comprising a vital sign.

13. The apparatus of claim 1, further comprising a memory, wherein said memory is configured to store an electronic medical record and said display device is configured to display at least a portion of said electronic medical record.

14. The apparatus of claim 10, further comprising a memory, wherein said memory is configured for storing a signal representative of at least a portion of the plurality of corresponding electrical signals generated by the plurality of sensors.

15. An apparatus for acquiring and processing physiological sounds comprising:
    a port configured to be operatively coupled to a sensor, said sensor configured to convert a first physiological sound into an electrical signal;
    a corresponding analogue to digital converter operatively coupled to the sensor, said analogue to digital converter configured to convert at least a portion of said electrical signal into a stream of digital data; and
    a display device configured to display a plurality of icons, wherein each icon of said plurality of icons displayed respectively correspond to at least one operation of a plurality of operations that said apparatus is configured to perform, wherein said plurality of icons displayed on said display device is configured for customization by a user through insertion of an additional icon in said plurality of icons displayed, and wherein the apparatus is configured to initiate a recording of a signal representative of a second physiological sound, by interaction of said user with at least one icon in said plurality of icons displayed, that is received over a network.

16. The apparatus of claim 15, further comprising a serial to parallel converter operatively coupled to said analogue to digital converter, said serial to parallel converter configured to convert at least a portion of the stream of digital data into a parallel output.

17. The apparatus of claim 16, further comprising a parallel to serial converter operatively coupled to the serial to parallel converter and configured to convert at least a portion of said parallel output into a transmission serial output, wherein said apparatus is configured to transmit said transmission serial output over the network.

18. The apparatus of claim 17, wherein the network is a wireless network, the apparatus further comprising a digital to analogue converter configured to convert at least a portion of said transmission serial output into an analogue signal for transmission over said wireless network.

19. The apparatus of claim 15 further comprising a memory, wherein said memory is configured to store an electronic medical record and said display device is configured to display at least a portion of said electronic medical record.

20. The apparatus of claim 15, wherein said display device is configured to display information comprising a vital sign.

\* \* \* \* \*